United States Patent [19]
Pandey et al.

[11] Patent Number: 5,854,278
[45] Date of Patent: Dec. 29, 1998

[54] PREPARATION OF CHLORINATED PACLITAXEL ANALOGUES AND USE THEREOF AS ANTITUMOR AGENTS

[75] Inventors: Ramesh C. Pandey, Highland Park; Luben K. Yankov, Edison; Raghu Nair, Bridgewater; Alex Poulev, Highland Park, all of N.J.

[73] Assignee: Xechem International, Inc., New Brunswick, N.J.

[21] Appl. No.: 672,397

[22] Filed: May 29, 1996

Related U.S. Application Data

[63] Continuation-in-part of Ser. No. 571,427, Dec. 13, 1995.

[51] Int. Cl.$^6$ .................. A61K 31/335; C07D 305/14
[52] U.S. Cl. ................ 514/449; 549/510; 549/511
[58] Field of Search ................... 549/510, 511; 514/449

[56] References Cited

U.S. PATENT DOCUMENTS

| | | | |
|---|---|---|---|
| 4,814,470 | 3/1989 | Colin et al. | 514/449 |
| 4,924,011 | 5/1990 | Denis et al. | 549/510 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,136,060 | 8/1992 | Holton | 549/510 |
| 5,157,049 | 10/1992 | Haugwitz et al. | 514/449 |
| 5,175,315 | 12/1992 | Holton | 549/510 |
| 5,194,635 | 3/1993 | Kingston et al. | 549/430 |
| 5,200,534 | 4/1993 | Rao | 549/510 |
| 5,202,448 | 4/1993 | Carver et al. | 549/510 |
| 5,227,400 | 7/1993 | Holton et al. | 514/444 |
| 5,229,526 | 7/1993 | Holton | 549/213 |
| 5,243,045 | 9/1993 | Holton et al. | 544/60 |
| 5,248,796 | 9/1993 | Chen et al. | 549/510 |
| 5,250,683 | 10/1993 | Holton et al. | 544/60 |
| 5,250,722 | 10/1993 | Bombardelli et al. | 560/104 |
| 5,254,580 | 10/1993 | Chen et al. | 514/449 |
| 5,254,703 | 10/1993 | Holton | 549/510 |
| 5,272,171 | 12/1993 | Ueda et al. | 514/449 |
| 5,274,124 | 12/1993 | Holton | 549/214 |
| 5,278,324 | 1/1994 | Kingston et al. | 549/510 |
| 5,279,949 | 1/1994 | Nair | 435/123 |
| 5,283,253 | 2/1994 | Holton et al. | 514/444 |
| 5,284,864 | 2/1994 | Holton et al. | 514/449 |
| 5,284,865 | 2/1994 | Holton et al. | 514/449 |
| 5,294,637 | 3/1994 | Chen et al. | 514/449 |
| 5,296,506 | 3/1994 | Kingston et al. | 514/449 |
| 5,300,638 | 4/1994 | Farina et al. | 540/357 |
| 5,310,672 | 5/1994 | Wann et al. | 435/240 |
| 5,319,112 | 6/1994 | Kingston et al. | 549/510 |
| 5,334,732 | 8/1994 | Murray et al. | 549/510 |
| 5,336,684 | 8/1994 | Murray et al. | 514/449 |
| 5,336,785 | 8/1994 | Holton | 549/214 |
| 5,338,872 | 8/1994 | Holton et al. | 549/510 |
| 5,412,092 | 5/1995 | Rey et al. | 540/200 |
| 5,470,866 | 11/1995 | Kingston et al. | 514/376 |
| 5,473,055 | 12/1995 | Mongelli et al. | 530/329 |
| 5,475,011 | 12/1995 | Ojima et al. | 514/320 |
| 5,475,120 | 12/1995 | Rao | 549/510 |

OTHER PUBLICATIONS

Rimoldi et al, J. Nat. Product, 1996, vol. 59(2), 167–168.
"Cephalomannine; a New Antitumor Alkaloid from *Cephalotaxus mannii*" by Powell et al., J.C.S. Chem. Comm., pp. 102–105 (1979).
"Biologically Active Taxol Analogues With Depleted A–Ring Side Chain Substituents and Variable C–2' Configurations" by Swindell et al., J.Med.Chem 34 (37:1176–1184 (1991)).

*Primary Examiner*—Ba K. Trinh
*Attorney, Agent, or Firm*—Duane, Morris & Heckscher LLP

[57] ABSTRACT

Provided are novel paclitaxel analogues which are selectively chlorinated stereospecific derivatives of cephalomannine and 7-epi-cephalomannine having paclitaxel-like antitumor efficacy, methods for their preparation and methods for treating tumors with these compounds.

15 Claims, 33 Drawing Sheets

FIG. 12A (2"R,3"S)-Dichloro-cephalomannine
DATA SHEET

| | | | Mean Optical Densities | | | |
|---|---|---|---|---|---|---|
| | Time | | | Log10 Concentration | | |
| Panel/Cell Line | Zero | Ctrl | -8.3 | -7.3 | -6.3 | -5.3 | -4.3 |
| Leukemia | | | | | | | |
| CCRF-CEM | 0.279 | 1.202 | 1.168 | 1.171 | 0.895 | 0.941 | 0.758 |
| HL-60(TB) | 0.242 | 1.008 | 0.973 | 0.533 | 0.478 | 0.462 | 0.629 |
| K-562 | 0.141 | 1.261 | 1.094 | 1.089 | 0.538 | 0.437 | 0.463 |
| MOLT-4 | 0.567 | 2.023 | 1.997 | 2.326 | 1.327 | 0.868 | 0.661 |
| RPMI-8226 | 1.074 | 1.862 | 1.807 | 1.449 | 0.838 | 0.900 | 0.738 |
| SR | 0.468 | 1.657 | 1.518 | 0.920 | 0.656 | 0.523 | 0.421 |
| Non-Small Cell Lung Cancer | | | | | | | |
| A549/ATCC | 0.328 | 1.623 | 1.613 | 1.504 | 0.865 | 0.514 | 0.354 |
| EKVX | 0.315 | 0.732 | 0.677 | 0.658 | 0.542 | 0.422 | 0.396 |
| HOP-62 | 0.433 | 0.843 | 0.757 | 0.759 | 0.607 | 0.531 | 0.440 |
| HOP-92 | 0.312 | 1.008 | 0.873 | 0.881 | 0.624 | 0.607 | 0.394 |
| NCI-H226 | 0.476 | 1.001 | 0.884 | 0.822 | 0.555 | 0.540 | 0.518 |
| NCI-H23 | 0.546 | 1.544 | 1.555 | 1.399 | 0.728 | 0.609 | 0.409 |
| NCI-H322M | 0.405 | 1.384 | 1.370 | 1.326 | 0.700 | 0.569 | 0.395 |
| NCI-H522 | 0.224 | 0.454 | 0.464 | 0.409 | 0.214 | 0.114 | 0.135 |
| Colon Cancer | | | | | | | |
| COLO 205 | 0.329 | 1.210 | 1.239 | 1.109 | 0.403 | 0.247 | 0.090 |
| HCC-2998 | 0.137 | 0.627 | 0.611 | 0.375 | 0.132 | 0.051 | 0.002 |
| HCT-116 | 0.163 | 1.528 | 1.503 | 0.701 | 0.202 | 0.147 | 0.045 |
| HT-15 | 0.210 | 1.533 | 1.493 | 1.529 | 1.305 | 0.446 | 0.156 |
| HT29 | 0.132 | 0.881 | 0.797 | 0.420 | 0.141 | 0.096 | 0.038 |
| KM12 | 0.100 | 0.722 | 0.595 | 0.446 | 0.180 | 0.139 | 0.124 |
| SW-620 | 0.176 | 1.064 | 0.989 | 0.673 | 0.192 | 0.168 | 0.105 |

| FIG. 12 | |
|---|---|
| FIG.12A | FIG.12B |
| FIG.12C | FIG.12D |
| FIG.12E | |

FIG. 12B

(2"R,3"S)-Dichloro-cephalomannine DATA SHEET

Log10 Concentration

| Percent Growth | | | | | | | GI50 | TGI | LC50 |
|---|---|---|---|---|---|---|---|---|---|
| -8.3 | -7.3 | -6.3 | -5.3 | -4.3 | | | | | |
| 96 | 97 | 67 | 72 | 52 | | | >5.00E-05 | >5.00E-05 | >5.00E-05 |
| 95 | 38 | 31 | 29 | 51 | | | . | >5.00E-05 | >5.00E-05 |
| 85 | 85 | 35 | 26 | 29 | | | 2.53E-07 | >5.00E-05 | >5.00E-05 |
| 98 | 121 | 52 | 21 | 6 | | | 5.88E-07 | >5.00E-05 | >5.00E-05 |
| 93 | 48 | -22 | -16 | -31 | | | 4.42E-08 | 2.41E-07 | >5.00E-05 |
| 88 | 38 | 16 | 5 | -10 | | | 2.89E-08 | 1.03E-05 | >5.00E-05 |
| 99 | 91 | 41 | 14 | 2 | | | 3.35E-07 | >5.00E-05 | >5.00E-05 |
| 87 | 82 | 54 | 26 | 19 | | | 7.10E-07 | >5.00E-05 | >5.00E-05 |
| 79 | 79 | 42 | 24 | 2 | | | 3.12E-07 | >5.00E-05 | >5.00E-05 |
| 81 | 82 | 45 | 42 | 12 | | | 3.62E-07 | >5.00E-05 | >5.00E-05 |
| 78 | 66 | 15 | 12 | 8 | | | 1.02E-07 | >5.00E-05 | >5.00E-05 |
| 101 | 85 | 18 | 6 | -25 | | | 1.68E-07 | 7.94E-06 | >5.00E-05 |
| 99 | 94 | 30 | 17 | -2 | | | 2.44E-07 | 3.72E-05 | >5.00E-05 |
| 105 | 80 | -5 | -49 | -40 | | | 1.14E-07 | 4.40E-07 | >5.00E-05 |
| 103 | 88 | 8 | -25 | -73 | | | 1.51E-07 | 8.96E-07 | 1.67E-05 |
| 97 | 49 | -4 | -63 | -98 | | | 4.66E-08 | 4.19E-07 | 3.00E-06 |
| 98 | 39 | 3 | -10 | -72 | | | 3.30E-08 | 8.40E-07 | 2.19E-05 |
| 97 | 100 | 83 | 18 | -26 | | | 1.60E-06 | 1.28E-05 | >5.00E-05 |
| 89 | 38 | 1 | -28 | -71 | | | 2.95E-08 | 5.48E-07 | 1.63E-05 |
| 79 | 56 | 13 | 6 | 4 | | | 6.78E-08 | >5.00E-05 | >5.00E-05 |
| 92 | 56 | 2 | -5 | -41 | | | 6.44E-08 | 9.47E-07 | >5.00E-05 |

*(2"R,3"S)-Dichloro-cephalomannine*

DATA SHEET

| | | | | | | | |
|---|---|---|---|---|---|---|---|
| 90. | 81 | 32 | 7 | -20 | 2. 15-07E | 8. 85E-06 | >5. 00E-05 |
| 97 | 91 | 34 | -55 | -65 | 2. 63E-07 | 1. 21E-06 | 4. 36E-06 |
| 88 | 76 | 16 | -55 | -66 | 1. 35E-07 | 8. 34E-07 | 4. 30E-06 |
| 90 | 77 | 28 | 9 | 0 | 1. 78E-07 | >5. 00E-05 | >5. 00E-05 |
| 78 | 75 | 39 | -31 | -33 | 2. 47E-07 | 1. 80E-06 | >5. 00E-05 |
| 96 | 78 | 25 | -8 | -31 | 1. 70E-07 | 2. 85E-06 | >5. 00E-05 |
| | | | | | | | |
| 92 | 66 | 21 | 11 | -62 | 1. 13E-07 | 7. 01E-06 | 3. 43E-05 |
| 103 | 59 | 18 | 3 | -30 | 8. 40E-08 | 5. 98E-06 | >5. 00E-05 |
| 96 | 84 | 18 | -27 | -75 | 1. 63E-07 | 1. 26E-06 | 1. 51E-05 |
| 92 | 75 | 63 | 5 | -53 | 8. 25E-07 | 6. 07E-06 | 4. 39E-05 |
| 106 | 47 | 11 | 21 | -88 | 4. 43E-08 | 7. 83E-06 | 2. 24E-05 |
| 82 | 50 | 27 | 20 | -64 | 5. 23E-87 | 8. 68E-06 | 3. 43E-05 |
| 98 | 68 | 28 | 26 | -58 | 1. 41E-07 | 1. 02E-05 | 4. 06E-05 |
| | | | | | | | |
| 93 | 62 | 26 | 10 | -4 | 1. 07E-07 | 2. 62E-05 | >5. 00E-05 |
| 78 | 68 | -13 | -16 | -49 | 8. 33E-08 | 3. 44E-07 | >5. 00E-05 |
| 99 | 96 | 68 | 52 | 24 | 5. 83E-06 | >5. 00E-05 | >5. 00E-05 |
| 91 | 90 | 25 | -4 | -58 | 2. 06E-07 | 3. 62E-06 | 3. 57E-05 |
| 99 | 97 | 58 | -29 | -32 | 6. 19E-07 | 2. 33E-06 | >5. 00E-05 |
| 90 | 86 | 16 | -18 | -20 | 1. 63E-07 | 1. 44E-06 | >5. 00E-05 |

*FIG. 12D*

*(2"R,3"S)-Dichloro-cephalomannine*

DATA SHEET

| | | | | | | | |
|---|---|---|---|---|---|---|---|
| Renal Cancer | | | | | | | |
| 786-0 | 0.185 | 0.955 | 0.909 | 0.900 | 0.475 | 0.182 | 0.100 |
| ACHN | 0.130 | 0.638 | 0.554 | 0.523 | 0.324 | 0.308 | 0.155 |
| CAKI-1 | 0.372 | 1.053 | 1.038 | 1.125 | 0.921 | 0.758 | 0.481 |
| SN12C | 0.236 | 0.755 | 0.728 | 0.736 | 0.395 | 0.407 | 0.272 |
| TK-10 | 0.145 | 0.654 | 0.585 | 0.558 | 0.397 | 0.313 | 0.188 |
| UO-31 | 1.296 | 2.021 | 2.018 | 2.067 | 1.999 | 1.265 | 0.829 |
| Prostate Cancer | | | | | | | |
| PC-3 | 0.531 | 1.953 | 1.852 | 1.860 | 0.830 | 0.511 | 0.467 |
| DU-145 | 0.366 | 1.046 | 1.067 | 1.028 | 0.557 | 0.310 | 0.248 |
| Breast Cancer | | | | | | | |
| MCF7 | 0.232 | 1.214 | 1.149 | 0.768 | 0.345 | 0.327 | 0.202 |
| MCF7/ADR-RES | 0.757 | 1.202 | 1.167 | 1.217 | 1.062 | 0.717 | 0.263 |
| MDA-MB-231/ATCC | 0.380 | 0.774 | 0.779 | 0.726 | 0.580 | 0.497 | 0.244 |
| HS 578T | 0.346 | 0.756 | 0.637 | 0.616 | 0.382 | 0.268 | 0.226 |
| MDA-MB-435 | 0.321 | 1.366 | 1.151 | 0.361 | 0.096 | 0.108 | 0.155 |
| MDA-N | 0.254 | 1.152 | 1.066 | 0.299 | 0.050 | 0.070 | 0.086 |
| BT-549 | 0.373 | 0.981 | 0.907 | 0.812 | 0.607 | 0.439 | 0.325 |
| T-47D | 0.525 | 1.295 | 1.311 | 1.207 | 0.858 | 0.833 | 0.722 |

*FIG. 12E*

(2"R,3"S)–Dichloro-cephalomannine
DATA SHEET

| | | | | | | | |
|---|---|---|---|---|---|---|---|
| 94 | 93 | 38 | -2 | | 2.98E-07 | 4.48E-06 | >5.00E-05 |
| 83 | 77 | 38 | 35 | -46 | 2.50E-07 | >5.00E-05 | >5.00E-05 |
| 98 | 111 | 80 | 57 | 5 | 7.26E-06 | >5.00E-05 | >5.00E-05 |
| 95 | 96 | 31 | 33 | 16 | 2.53E-07 | >5.00E-05 | >5.00E-05 |
| 86 | 81 | 49 | 33 | 7 | 4.80E-07 | >5.00E-05 | >5.00E-05 |
| 100 | 106 | 97 | -2 | 8 | 1.49E-06 | 4.73E-06 | >5.00E-05 |
| | | | | -36 | | | |
| 93 | 94 | 21 | -4 | -12 | 1.99E-07 | 3.50E-06 | >5.00E-05 |
| 103 | 97 | 28 | -15 | -32 | 2.41E-07 | 2.22E-06 | >5.00E-05 |
| 93 | 55 | 11 | 10 | -13 | 6.39E-08 | 1.34E-05 | >5.00E-05 |
| 92 | 103 | 69 | -5 | -65 | 8.95E-07 | 4.24E-06 | 2.78E-05 |
| 101 | 88 | 51 | 30 | -36 | 5.43E-07 | 1.42E-05 | >5.00E-05 |
| 71 | 66 | 9 | -23 | -35 | 9.45E-08 | 9.47E-07 | >5.00E-05 |
| 79 | 4 | -70 | -67 | -52 | 1.23E-08 | 5.64E-08 | 2.68E-07 |
| 90 | 5 | -80 | -72 | -66 | 1.49E-08 | 5.72E-08 | 2.21E-07 |
| 88 | 72 | 38 | 11 | -13 | 2.27E-07 | 1.42E-05 | >5.00E-05 |
| 102 | 89 | 43 | 40 | 26 | 3.55E-07 | >5.00E-05 | >5.00E-05 |

FIG. 12F

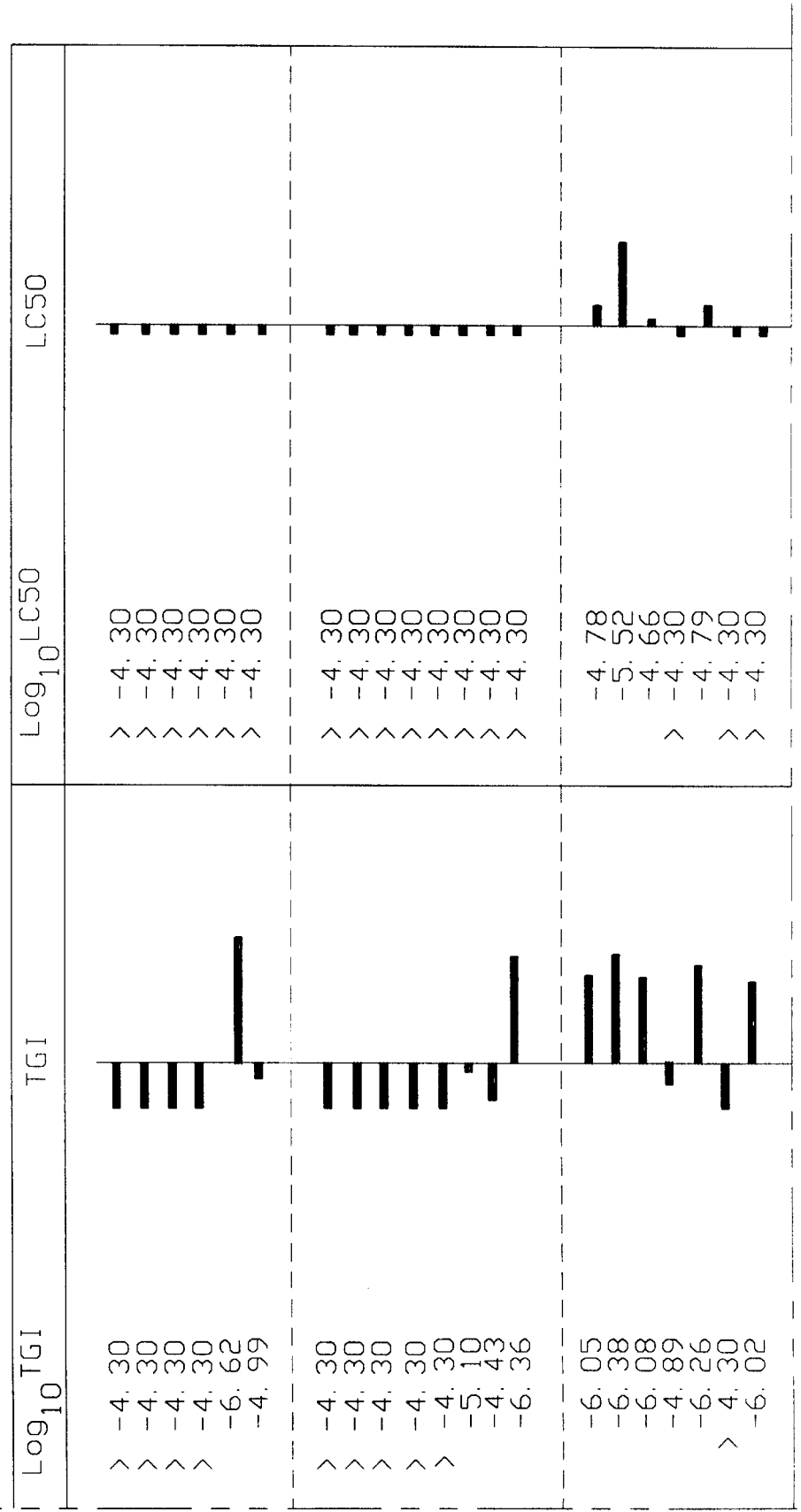
FIG. 13B  (2"R,3"S)-Dichloro-cephalomannine MEAN GRAPHS

FIG. 14

| FIG.14A | FIG.14B |
|---|---|
| FIG.14C | FIG.14D |
| FIG.14E | FIG.14F |

FIG. 14A (2"S,3"R)-Dichloro-cephalomannine
DATA SHEET

| Panel/Cell Line | Time Zero | Ctrl | -8.3 | -7.3 | -6.3 | -5.3 | -4.3 |
|---|---|---|---|---|---|---|---|
| Leukemia | | | | | | | |
| CCRF-CEM | 0.279 | 1.202 | 1.304 | 0.750 | 0.434 | 0.341 | 0.290 |
| HL-60(TB) | 0.242 | 1.008 | 1.066 | 0.423 | 0.242 | 0.189 | 0.241 |
| K-562 | 0.141 | 1.261 | 1.383 | 0.387 | 0.340 | 0.182 | 0.189 |
| MOLT-4 | 0.567 | 2.023 | 1.971 | 1.487 | 0.909 | 0.646 | 0.375 |
| RPMI-8226 | 1.074 | 1.862 | 1.878 | 0.851 | 0.672 | 0.590 | 0.458 |
| SR | 0.468 | 1.657 | 1.206 | 0.613 | 0.483 | 0.338 | 0.280 |
| Non-Small Cell Lung Cancer | | | | | | | |
| A549/ATCC | 0.328 | 1.623 | 1.680 | 1.356 | 0.872 | 0.484 | 0.350 |
| EKVX | 0.315 | 0.732 | .710 | 0.702 | 0.568 | 0.427 | 0.331 |
| HOP-62 | 0.433 | 0.843 | 0.769 | 0.773 | 0.620 | 0.523 | 0.391 |
| HOP-92 | 0.312 | 1.008 | 0.919 | 0.869 | 0.690 | 0.678 | 0.381 |
| NCI-H226 | 0.476 | 1.001 | 0.948 | 0.860 | 0.635 | 0.593 | 0.508 |
| NCI-H23 | 0.546 | 1.544 | 1.640 | 1.350 | 0.774 | 0.626 | 0.396 |
| NCI-H322M | 0.405 | 1.384 | 1.366 | 1.167 | 0.704 | 0.542 | 0.451 |
| NCI-H522 | 0.224 | 0.454 | 0.464 | 0.378 | 0.205 | 0.093 | 0.137 |
| Colon Cancer | | | | | | | |
| COLO 205 | 0.329 | 1.210 | 1.161 | 0.707 | 0.266 | 0.133 | 0.041 |
| HCC-2998 | 0.137 | 0.627 | 0.649 | 0.434 | 0.176 | 0.058 | 0.023 |
| HCT-116 | 0.163 | 1.528 | 1.331 | 0.474 | 0.197 | 0.097 | 0.025 |
| HCT-15 | 0.210 | 1.533 | 1.397 | 1.308 | 1.130 | 0.283 | 0.186 |
| HT29 | 0.132 | 0.881 | 0.831 | 0.386 | 0.161 | 0.108 | 0.036 |
| KM12 | 0.100 | 0.722 | 0.613 | 0.357 | 0.306 | 0.246 | 0.183 |
| SW-620 | 0.176 | 1.064 | 0.932 | 0.426 | 0.161 | 0.131 | 0.076 |

Mean Optical Densities — Log10 Concentration

FIG. 14B (2"S,3"R)-Dichloro-cephalomannine
DATA SHEET

Log10 Concentration

| Percent Growth | | | | | | | | |
|---|---|---|---|---|---|---|---|---|
| -8.3 | -7.3 | -6.3 | -5.3 | -4.3 | GI50 | TGI | LC50 |
| 111 | 51 | 17 | 7 | 1 | 5.36E-08 | >5.00E-05 | >5.00E-05 |
| 108 | 24 | 0 | -22 | -1 | 2.42E-08 | 4.90E-07 | >5.00E-05 |
| 111 | 31 | 18 | 4 | 4 | 2.89E-08 | >5.00E-05 | >5.00E-05 |
| 96 | 63 | 23 | 5 | -34 | 1.07E-07 | 6.88E-06 | >5.00E-05 |
| 102 | -21 | -37 | -45 | -57 | 1.33E-08 | 3.38E-08 | 1.26E-05 |
| 62 | 12 | 1 | -28 | -40 | 8.71E-09 | >5.00E-05 | >5.00E-05 |
| | | | | | | | |
| 104 | 79 | 42 | 12 | 2 | 3.05E-07 | >5.00E-05 | >5.00E-05 |
| 95 | 93 | 61 | 27 | 4 | 1.03E-06 | >5.00E-05 | >5.00E-05 |
| 82 | 83 | 45 | 22 | -10 | 3.78E-07 | 2.45E-05 | >5.00E-05 |
| 87 | 80 | 54 | 53 | 10 | 5.78E-06 | >5.00E-05 | >5.00E-05 |
| 90 | 73 | 30 | 22 | 6 | 1.73E-07 | <5.00E-05 | >5.00E-05 |
| 110 | 81 | 23 | 8 | -28 | 1.69E-07 | 8.38E-06 | >5.00E-05 |
| 98 | 78 | 30 | 14 | 5 | 1.94E-07 | >5.00E-05 | >5.00E-05 |
| 105 | 67 | -8 | -58 | -39 | 8.42E-08 | 3.86E-07 | . |
| | | | | | | | |
| 94 | 43 | -19 | -60 | -88 | 3.63E-08 | 2.45E-07 | 2.87E-06 |
| 104 | 61 | 8 | -58 | -83 | 7.97E-08 | 6.61E-07 | 3.82E-06 |
| 86 | 23 | 2 | -41 | -84 | 1.84E-08 | 5.70E-07 | 8.13E-06 |
| 90 | 83 | 70 | 5 | -12 | 1.01E-06 | 1.04E-05 | >5.00E-05 |
| 93 | 34 | 4 | -19 | -72 | 2.68E-08 | 7.40E-07 | 1.92E-05 |
| 82 | 41 | 33 | 23 | 13 | 3.07E-08 | >5.00E-05 | >5.00E-05 |
| 85 | 28 | -9 | -26 | -57 | 2.07E-08 | 2.89E-07 | 3.01E-05 |

(2"S,3"R)-Dichloro-cephalomannine
DATA SHEET

| | | | | | | |
|---|---|---|---|---|---|---|
| CNS Cancer | | | | | | |
| SF-268 | 0.373 | 1.084 | 0.990 | 0.838 | 0.644 | 0.483 | 0.336 |
| SF-295 | 0.415 | 1.290 | 1.251 | 1.237 | 0.620 | 0.168 | 0.085 |
| SF-539 | 0.491 | 1.440 | 1.357 | 1.076 | 0.605 | 0.258 | 0.119 |
| SNB-19 | 0.276 | 0.908 | 0.852 | 0.749 | 0.514 | 0.344 | 0.297 |
| SNB-75 | 0.443 | 0.820 | 0.775 | 0.764 | 0.660 | 0.365 | 0.387 |
| U251 | 0.293 | 1.169 | 1.087 | 0.883 | 0.521 | 0.264 | 0.135 |
| Melanoma | | | | | | |
| LOX IMVI | 0.282 | 1.700 | 1.517 | 1.056 | 0.529 | 0.292 | 0.032 |
| MALME-3M | 0.445 | 0.783 | 0.848 | 0.675 | 0.549 | 0.487 | 0.241 |
| M14 | 0.276 | 1.072 | 1.022 | 0.844 | 0.440 | 0.159 | 0.050 |
| SK-MEL-2 | 1.225 | 1.848 | 1.672 | 1.604 | 1.331 | 1.086 | 0.455 |
| SK-MEL-5 | 0.135 | 1.002 | 0.923 | 0.491 | 0.211 | 0.269 | 0.002 |
| UACC-257 | 0.175 | 0.773 | 0.771 | 0.604 | 0.508 | 0.421 | 0.135 |
| UACC-62 | 0.473 | 1.691 | 1.616 | 1.202 | 0.929 | 0.839 | 0.114 |
| Ovarian Cancer | | | | | | |
| IGROVI | 0.410 | 1.309 | 1.209 | 0.981 | 0.699 | 0.613 | 0.428 |
| OVCAR-3 | 0.529 | 1.393 | 1.246 | 0.945 | 0.405 | 0.357 | 0.221 |
| OVCAR-4 | 0.604 | 1.650 | 1.625 | 1.526 | 1.354 | 1.181 | 0.909 |
| OVCAR-5 | 0.612 | 0.971 | 0.972 | 0.945 | 0.718 | 0.598 | 0.147 |
| OVCAR-8 | 1.032 | 1.747 | 1.876 | 1.603 | 0.935 | 0.868 | 0.431 |
| SK-OV-3 | 0.689 | 1.198 | 1.145 | 1.100 | 0.704 | 0.585 | 0.531 |

FIG. 14C (2"S,3"R)-Dichloro-cephalomannine
DATA SHEET

| | | | | | | |
|---|---|---|---|---|---|---|
| 87 | 65 | 38 | 15 | -10 | 1.83E-07 | 20.3E-05 | >5.00E-05 |
| 96 | 94 | 23 | -60 | -79 | 2.10E-07 | 9.57E-07 | 3.84E-06 |
| 91 | 62 | 12 | -47 | -76 | 8.57E-08 | 7.95E-07 | 6.15E-06 |
| 91 | 75 | 38 | 11 | 3 | 2.33E-07 | >5.00E-05 | >5.00E-05 |
| 88 | 85 | 58 | -18 | -13 | 6.29E-07 | 2.91E-06 | >5.00E-05 |
| 91 | 67 | 26 | -10 | -54 | 1.32E-07 | 2.63E-06 | 4.04E-05 |
| 87 | 55 | 17 | 1 | -88 | 6.66E-08 | 5.09E-06 | 1.85E-05 |
| 119 | 68 | 31 | 12 | -46 | 1.51E-07 | 8.12E-06 | >5.00E-05 |
| 94 | 71 | 21 | -43 | -82 | 1.31E-07 | 1.06E-06 | 7.73E-06 |
| 72 | 61 | 17 | -11 | -63 | 8.87E-08 | 1.99E-06 | 2.82E-05 |
| 91 | 41 | 9 | 15 | -100 | 3.31E-08 | 6.80E-06 | 1.84E-05 |
| 100 | 72 | 56 | 41 | -23 | 1.23E-06 | 2.18E-05 | >5.00E-05 |
| 94 | 60 | 37 | 30 | -76 | 1.37E-07 | 9.61E-06 | 2.85E-05 |
| 89 | 63 | 32 | 23 | 2 | 1.34E-07 | >5.00E-05 | >5.00E-05 |
| 83 | 48 | -23 | -33 | -58 | 4.40E-08 | 2.35E-07 | 2.38E-05 |
| 98 | 88 | 72 | 55 | 29 | 7.92E-06 | >5.00E-05 | >5.00E-05 |
| 100 | 93 | 30 | -2 | -76 | 2.37E-07 | 4.21E-06 | 2.22E-05 |
| 118 | 80 | -9 | -16 | -58 | 1.08E-07 | 3.92E-07 | 3.20E-05 |
| 89 | 81 | 3 | -15 | -23 | 1.24E-07 | 7.19E-07 | >5.00E-05 |

*FIG. 14D*

*(2"S,3"R)–Dichloro–cephalomannine*

DATA SHEET

| | | | | | | | |
|---|---|---|---|---|---|---|---|
| Renal Cancer | | | | | | | |
| 786-0 | 0.185 | 0.955 | 0.948 | 0.866 | 0.391 | 0.179 | 0.120 |
| ACHN | 0.130 | 0.638 | 0.633 | 0.586 | 0.379 | 0.356 | 0.191 |
| CAKI-1 | 0.372 | 1.053 | 0.926 | 0.989 | 0.833 | 0.645 | 0.212 |
| SN12C | 0.236 | 0.755 | 0.753 | 0.674 | 0.440 | 0.393 | 0.249 |
| TK-10 | 0.145 | 0.654 | 0.646 | 0.533 | 0.384 | 0.296 | 0.246 |
| UO-31 | 1.296 | 2.021 | 2.016 | 2.066 | 2.012 | 1.205 | 0.752 |
| Prostate Cancer | | | | | | | |
| PC-3 | 0.531 | 1.953 | 1.882 | 1.606 | 0.751 | 0.498 | 0.453 |
| DU-145 | 0.366 | 1.046 | 1.103 | 0.990 | 0.524 | 0.260 | 0.251 |
| Breast Cancer | | | | | | | |
| MCF7 | 0.232 | 1.214 | 1.086 | 0.518 | 0.313 | 0.255 | 0.105 |
| MCF7/ADR-RES | 0.757 | 1.202 | 1.245 | 1.182 | 1.021 | 0.601 | 0.179 |
| MDA-MB-231/ATCC | 0.380 | 0.774 | 0.746 | 0.692 | 0.563 | 0.428 | 0.249 |
| HS 578T | 0.346 | 0.756 | 0.669 | 0.574 | 0.412 | 0.288 | 0.315 |
| MDA-MB-435 | 0.321 | 1.366 | 0.934 | 0.214 | 0.049 | 0.019 | 0.060 |
| MDA-N | 0.254 | 1.152 | 0.808 | 0.194 | 0.058 | 0.060 | 0.142 |
| BT-549 | 0.373 | 0.981 | 0.957 | 0.832 | 0.638 | 0.444 | 0.286 |
| T-47D | 0.525 | 1.295 | 1.315 | 1.136 | 0.848 | 0.818 | 0.733 |

*FIG. 14E*

(2"S,3"R)-Dichloro-cephalomannine
DATA SHEET

| | | | | | | | |
|---|---|---|---|---|---|---|---|
| 99 | 88 | 27 | -3 | -35 | 2.10E-07 | 3.90E-06 | >5.00E-05 |
| 99 | 90 | 49 | 44 | 12 | 4.70E-07 | >5.00E-05 | >5.00E-05 |
| 81 | 91 | 68 | 40 | -43 | 2.18E-06 | 1.52E-05 | >5.00E-05 |
| 100 | 84 | 39 | 30 | 2 | 2.91E-07 | >5.00E-05 | >5.00E-05 |
| 98 | 76 | 47 | 30 | 20 | 3.94E-07 | >5.00E-05 | >5.00E-05 |
| 99 | 106 | 99 | -7 | -42 | 1.45E-06 | 4.29E-06 | >5.00E-05 |
| 95 | 76 | 15 | -6 | -15 | 1.33E-07 | 2.57E-06 | >5.00E-05 |
| 108 | 92 | 23 | -29 | -31 | 2.03E-07 | 1.39E-06 | >5.00E-05 |
| 87 | 29 | 8 | 2 | -55 | 2.18E-08 | 5.49E-06 | 4.10E-05 |
| 110 | 96 | 59 | -21 | -76 | 6.55E-07 | 2.76E-06 | 1.68E-05 |
| 93 | 79 | 46 | 12 | -34 | 3.89E-07 | 9.16E-06 | >5.00E-05 |
| 79 | 56 | 16 | -17 | -9 | 6.93E-08 | 1.54E-06 | >5.00E-05 |
| 59 | -33 | -85 | -94 | -81 | 6.22E-09 | 2.17E-08 | 1.05E-07 |
| 62 | -23 | -77 | -76 | -44 | 6.86E-09 | 2.65E-08 | >5.00E-05 |
| 96 | 75 | 44 | 12 | -23 | 3.14E-07 | 1.08E-05 | >5.00E-05 |
| 103 | 79 | 42 | 38 | 27 | 3.05E-07 | >5.00E-05 | 5.00E-05 |

FIG. 14F

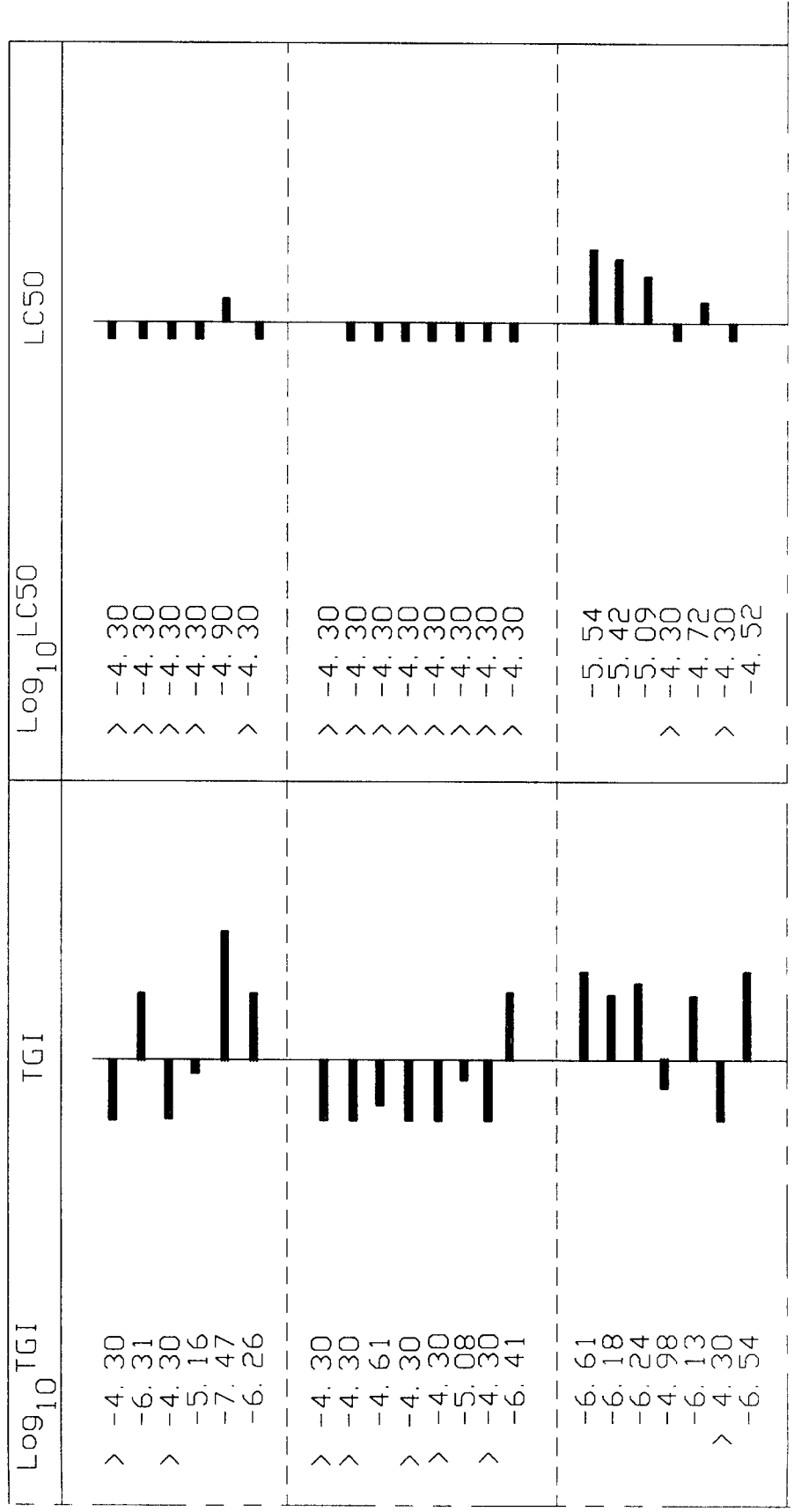
FIG. 15B  (2"S,3"R)-Dichloro-cephalomannine MEAN GRAPHS

PREPARATION OF CHLORINATED PACLITAXEL ANALOGUES AND USE THEREOF AS ANTITUMOR AGENTS

STATEMENT OF RELATED APPLICATIONS

This application is a continuation-in-part of U.S. application Ser. No. 08/571,427, filed Dec. 13, 1995, which is incorporated herein by reference.

FIELD OF THE INVENTION

This invention relates to paclitaxel analogues, namely 2", 3" -dichlorocephalomannines and corresponding 2", 3" -dichloro-7-epi-cephalomannine diastereomers; methods for their preparation, isolation and purification; and their use as effective antitumor agents and alternatives to paclitaxel in bioactivity testing.

BACKGROUND OF THE INVENTION

Cephalomannine is a natural product found in the bark of the Pacific yew tree *Taxus brevifolia* and other yew species, including *T. baccata, T. cuspidata, T. yunnanensis, T. chinensis, T. capitata, T. brownii* and T. dark green spreader. It can also be found in Cephalotaxus species such as *Cephalotaxus mannil*, as well as cultured plant cells and fungi.

Cephalomannine is most often present in combination with the well known and structurally similar taxane paclitaxel. The structures of cephalomannine and paclitaxel are set forth below.

Paclitaxel has been approved by the Food and Drug Administration for treatment of ovarian and breast cancer. It is also presently undergoing clinical trials for the treatment of other types of cancer. However, the supply of this valuable natural product is limited to a finite number of yew trees and other yew species containing relatively small amounts of paclitaxel. Therefore, alternate sources of paclitaxel as well as alternate compounds having paclitaxel-like antitumor activity are highly desired.

As set forth in U.S. application Ser. No. 08/571,427, filed Dec. 13, 1995, the entirety of which is incorporated herein by reference, a mixture of halogenated, e.g. dibrominated cephalomannines, have been shown to exhibit strong paclitaxel-like antitumor efficacy in vitro and in vivo in a variety of tumors, thereby providing a viable alternative to paclitaxel and paclitaxel derivatives such as Taxotere® (Rhône-Poulenc Rorer).

The chemical structures of both paclitaxel and cephalomannine contain eleven asymmetric carbon atoms, nine of which are in the taxane ring and two in the side chain attached to 13. Stereostructures of cephalomannine and paclitaxel are shown below.

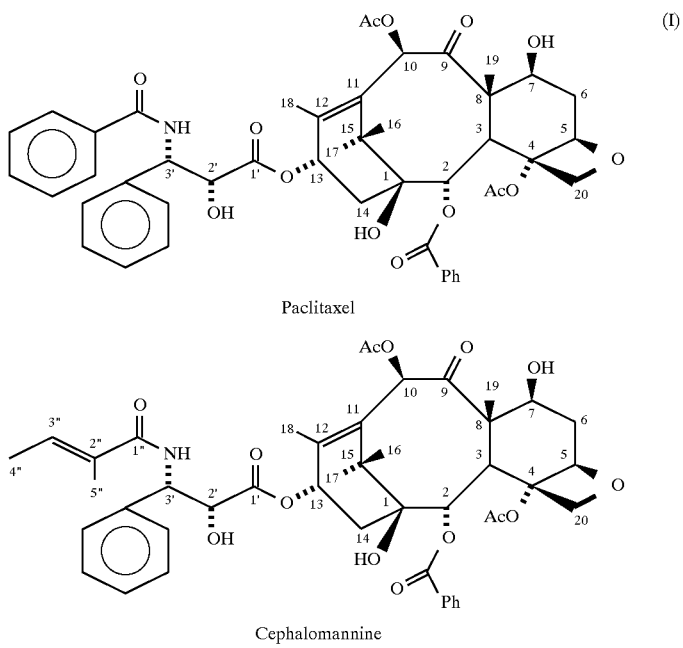

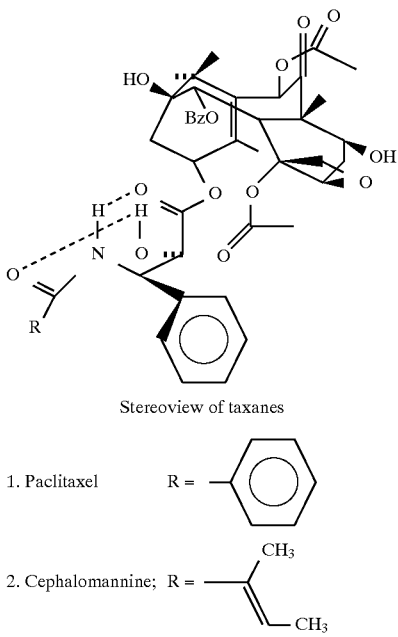

Stereoview of taxanes

1. Paclitaxel  R = —[phenyl]

2. Cephalomannine; R = —C(CH₃)=CH—CH₃

Additionally, the cephalomannine structure also contains an additional double bond in the carbon 13 side chain. This exocyclic double bond along with the number of stereocenters present in the structure of cephalomannine suggests the possibility for the existence of numerous stereoisomers of this taxane compound. For example, cephalomannine can be distributed in two isomeric forms wherein the hydroxyl group at carbon 13 is acylated with phenylisoserine acylated in amino group by either (Z)- or (E)-2-methyl-2-butenoic acid leading to (Z)- and (E)-cephalomannines, respectively. In addition, it is known that cephalomannine and paclitaxel can be epimerized at carbon 7, either thermally, during chromatographic procedures or in acidic or basic solutions. Miller, et al, *J. Org. Chem.*, 46: 1469 (1981); Chaudhary et al. *J. Org. Chem.*, 58:3978 (1993); and Wender, et al., CRC Press, Inc., Boca Raton, Fla., 1995, p. 130. Thus, during halogenation, each of these isomers can give rise to a mixture of diastereomeric products.

In accordance with this invention, four dichlorocephalomannine stereoisomers have now been isolated, with two derived from cephalomannine and the remaining two from 7-epi-cephalomannine, respectively. Most likely, the 7-epi-cephalomannine is produced from cephalomannine during the involved isolation and purification procedures. The individual diastereomers of 2", 3" -dichlorocephalomannine and corresponding dichloro-7-epi-cephalomannine diastereomers isolated and purified in accordance with this invention show strong paclitaxel-like antitumor activity in a variety of tumors.

SUMMARY OF THE INVENTION

The present invention provides novel selectively chlorinated derivatives of cephalomannine and 7-epi-cephalomannine having in vitro and in vivo paclitaxel-like antitumor activity, methods of preparation therefor as well as methods for treating tumors with these compounds. These chlorinated stereospecific cephalomannine derivatives are easily prepared in good yields from either complex mixtures comprising cephalomannine, paclitaxel and other taxanes, or from more refined sources of cephalomannine, by selective chlorination of the unsaturated 2", 3" side-chain of the cephalomannine molecule while leaving other parts of the molecule or other important taxane components in the mixture, such as paclitaxel, intact. Thus, chlorination of cephalomannine/7-epi-cephalomannine produces 2", 3" -dichlorocephalomannine/2", 3" -dichloro-7-epi-cephalomannine diastereomers which can be separated and purified by chromatographic procedures, and which show strong paclitaxel-like antitumor efficacy in a variety of tumors.

This invention is more fully described by the following detailed description of preferred embodiments with accompanying drawings and examples.

BRIEF DESCRIPTION OF THE DRAWINGS

FIG. 12 is a data sheet of in vitro testing results of the diastereomer (2 "R, 3"S) -dichlorocephalomannine (I) obtained from this invention in a screen of sixty human tumor cell lines.

FIG. 14 is a data sheet of in vitro testing results of the (2"S, 3"R) -dichlorocephalomannine diastereomer (II) obtained from this invention in a screen of sixty human tumor cell lines.

DETAILED DESCRIPTION OF PREFERRED EMBODIMENTS

Figure 1A:
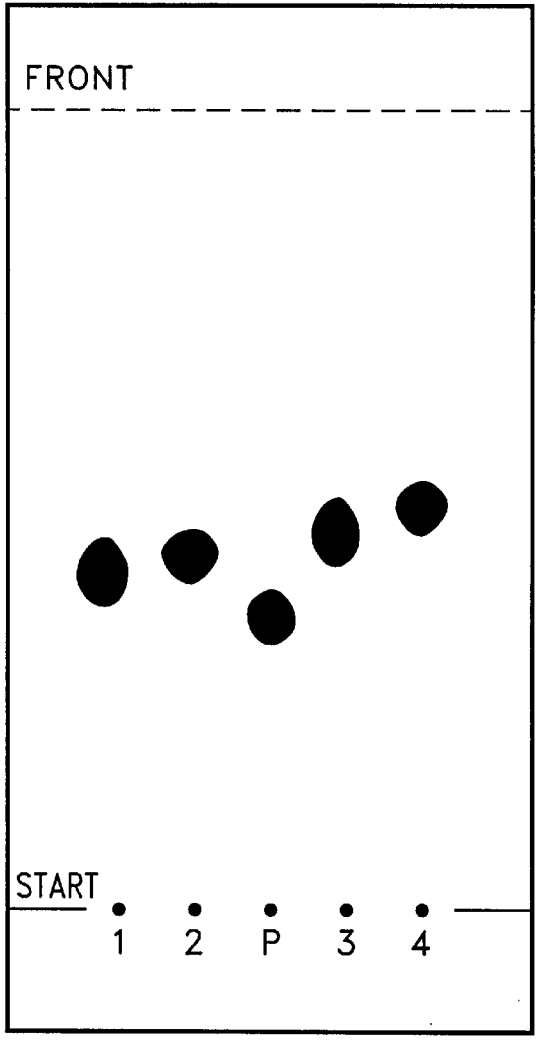
FIG. 1 is a TLC separation of dichlorocephalomannine (I and II) and (2"R,3"R) and (2"S,3"S)-dichlorocephalomannine diastereomers (III and IV) respectively.

The present invention provides isolated and purified 2",3"-dichlorocephalomannine and 2",3"-dichloro-7-epicephalomannine diasteromers, their preparation from cephalomannines and from unpurified, partially purified or purified mixtures of cephalomannine, paclitaxel and other taxanes. The diastereomers are prepared by reacting a mixture comprising cephalomannine/7-epi-cephalomannine with chlorine under conditions inclusive of a temperature and for a time effective to selectively chlorinate the unsaturated 2", 3" side-chain portion of cephalomannine and 7-epi-cephalomannine present, and then separating the resulting less polar dichlorocephalomannine and dichloro-7-epi-cephalomannine from diastereomers paclitaxel and other taxane compounds by standard chromatographic techniques and/or crystallization.

The method of this invention is advantageously independent of the concentration of cephalomannine and 7-epi-cephalomannine present in various complex mixtures of taxane compounds, and can utilize any source containing cephalomannine and 7-epi-cephalomannine as starting material. These sources include the bark from various Taxus species such as, for example, *Taxus brevifolia, Taxus baccata, Taxus yunnanensis, Taxus chinensis* and *Taxus wallichiana*, plant material such as needles and twigs from various Taxus and Cephalotaxus species, extracts of biomass containing a complex mixture of taxane type compounds, as well as in the downstream purification of cephalomannine and 7-epi-cephalomannine produced from sources such as cell cultures of Taxus/Cephalotaxus species and cephalomannine and 7-epi-cephalomannine producing fungi.

In a preferred method of this invention, a mixture of taxanes comprising cephalomannine and/or 7-epi-cephalomannine and paclitaxel, is treated with stoichiometric quantities of chlorine dissolved in an inert solvent, preferably carbon tetrachloride, chloroform, methylene chloride, or ethylene dichloride. In a typical treatment a mixture containing approximately 30% by weight cephalomannine in oxidized chloroform (containing three molar equivalents of chlorine) results in a quantitative yield of a mixture of 2", 3"-dichlorocephalomannine and the corresponding 7-epi-cephalomannine diastereomers(not shown). See Scheme I.

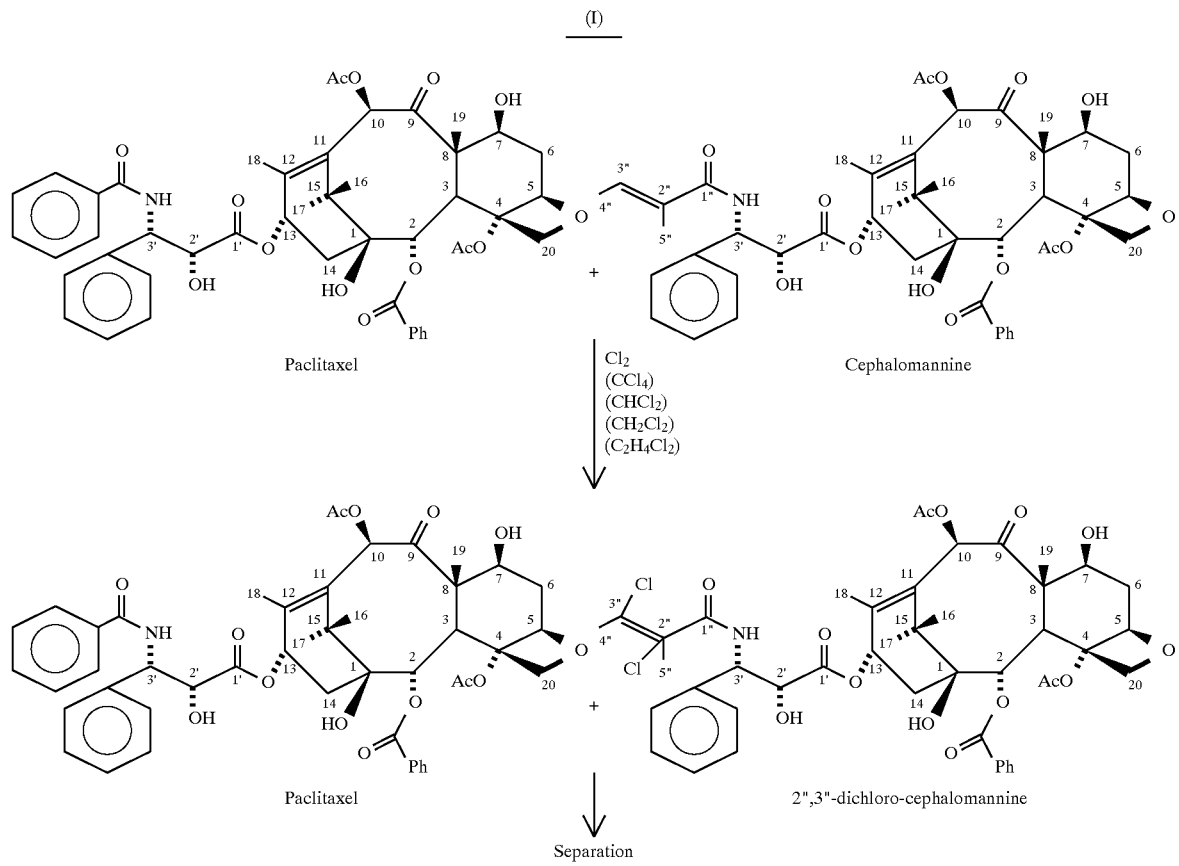

-continued (I)

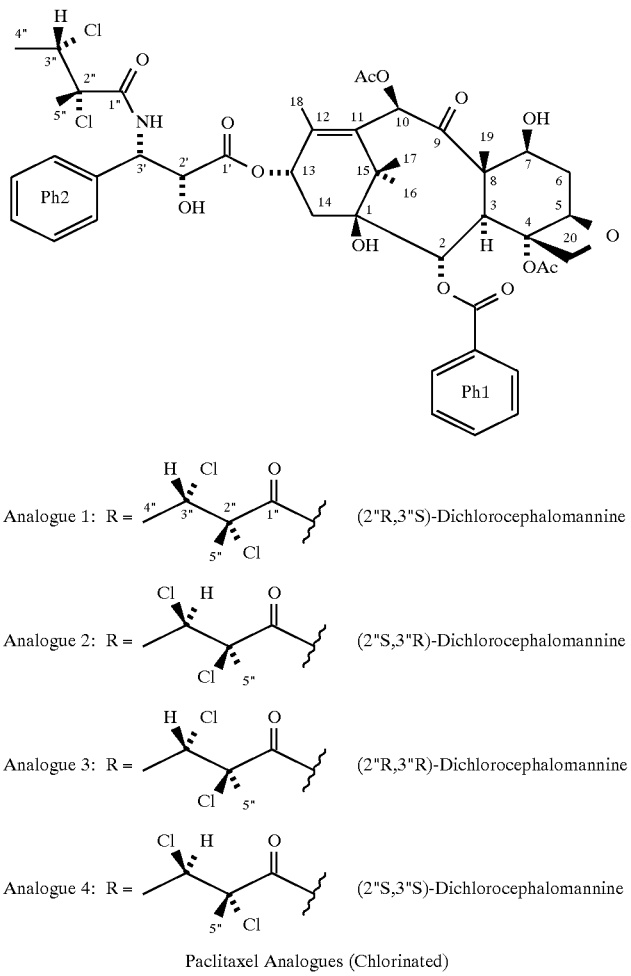

Paclitaxel Analogues (Chlorinated)

The pure diastereomers can be separated and their chemical structures elucidated using modern physicochemical methods (m.p., TLC, HPLC, UV, IR, NMR, MS).

In another example, chlorination of cephalomannine and 7-epi-cephalomannine is performed on a mixture containing approximately 30% cephalomannine, 50% paclitaxel, and 20% other impurities (as determined by HPLC analysis). The sample was dissolved in a preferred solvent (1,2-dichloroethane) and added dropwise to a cooled (2°–4° C.) solution of chlorine in 1,2-dichloroethane. The progress of the reaction was monitored by HPLC analysis. Cephalomannine was chlorinated completely within 2–3 hrs with no consumption of paclitaxel. The reaction mixture was washed with 1.0% sodium sulfite solution, water, dried with anhydrous sodium sulfate and concentrated to dry material. Dichlorocephalomannine and dichloro-7-epi-cephalomannine were separated from paclitaxel by recrystallization and further purified by HPLC of the mother liquor material.

For mixtures containing cephalomannine and from about 0.1% to about 99.5% paclitaxel, the process is similar to that described above. The mixture is first dissolved in an inert solvent, preferably a chlorinated solvent such as carbon tetrachloride, chloroform, 1,2-dichloroethane, or methylene chloride, and added to a cooled (e.g. 2°–4° C.) solution of chlorine (2–5 molar equivalents) in, say 1,2-dichloroethane. The mixture is stirred until the cephalomannine is completely chlorinated.

The chlorination process is most effective within the range of about –20° C. to about 20° C., and more preferably between about –5° and about 5° C., and preferably run in the dark. The chlorination reaction is also preferably conducted with a chlorine concentration in 1,2-dichloroethane in the range of from about 0.01- to about 0.1%. The progress of reaction can be conveniently monitored, for example, by HPLC analysis.

Cephalomannine and 7-epi-cephalomannine are chlorinated with high selectivity to diastereomers of 2",3"-dichlorocephalomannine and 2",3"-dichloro-7-epi-cephalomannine, respectively. The resulting mixture containing other taxane impurities is separated and purified using conventional methods such as chromatography and crystallization.

The molar equivalents of chlorine used is dependent on the cephalomannine and 7-epi-cephalomannine content and presence or absence of other unsaturated compounds. Generally, a less pure mixture, for example, a mixture containing large amounts of unsaturated taxanes relative to cephalomannine and 7-epi-cephalomannine, requires higher molar equivalents of chlorine to completely chlorinate all of the cephalomannine and 7-epi-cephalomannine present in the mixture. Structures are shown below of several unsaturated taxanes typically found in the presence of cephalomannine, 7-epi-cephalomannine and paclitaxel in plant extracts.

yields thereof. One might also expect the degradation of valuable taxanes, such as paclitaxel. However, in accordance with this invention, it has been unexpectedly found that

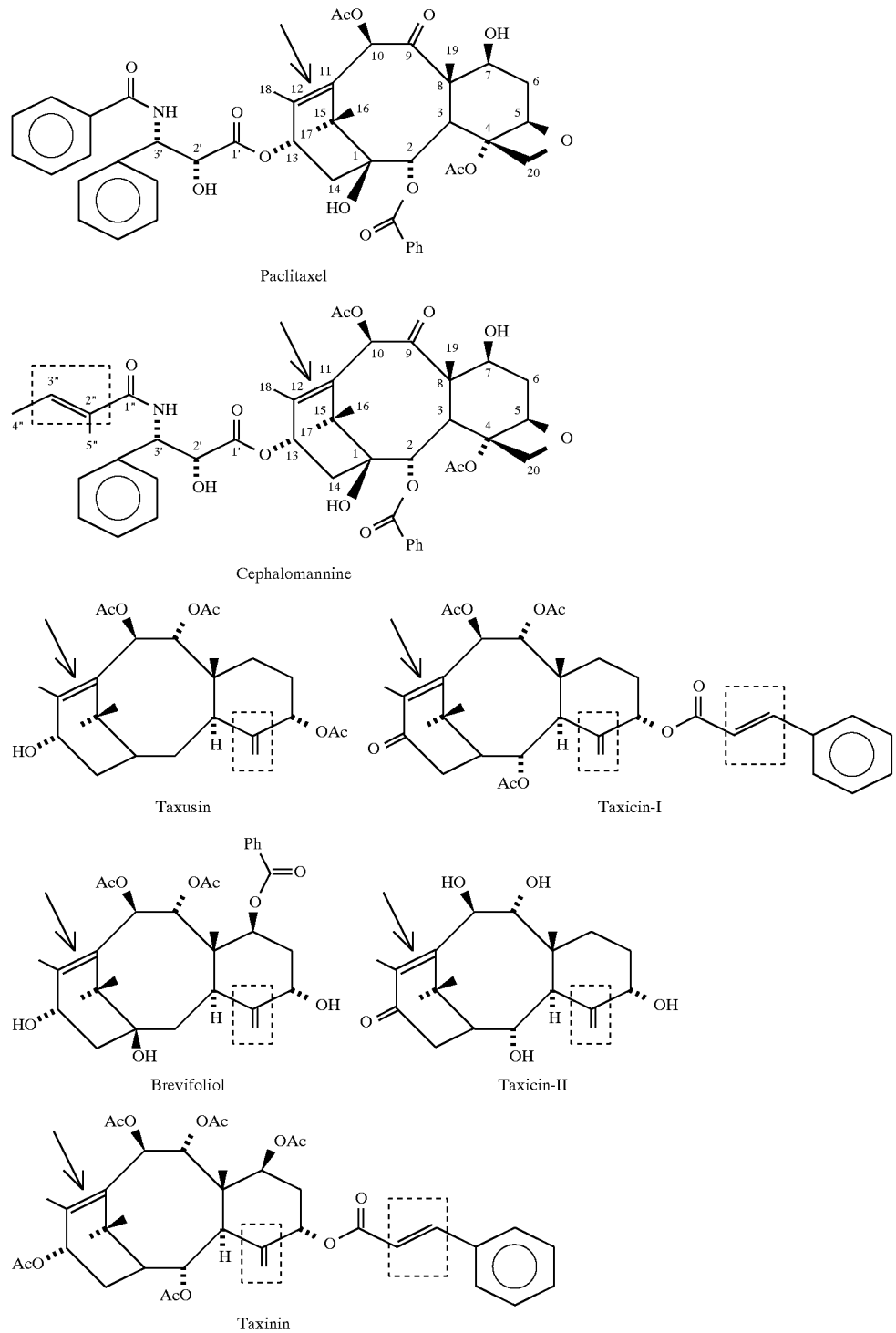

Conventional wisdom would lead one to expect that the use of chlorine in the presence of taxane compounds having several functional groups would result in undesired side reactions and deplete the concentration of cephalomannine and/or 7-epi-cephalomannine and chlorine without generating the desired dichlorocephalomannines or appreciable selectivity for chlorination of the 2",3"-side-chain double bond in cephalomannine and 7-epi-cephalomannine is very high under controlled conditions. In the process of this invention, paclitaxel is neither significantly degraded nor chlorinated during the reaction. Any undesired degradation during chlorination can be avoided and the proper conditions adjusted appropriately without undue experimentation by periodically monitoring the reaction, for example, by HPLC analysis.

The following examples are provided to illustrate preferred embodiments for selective chlorination of samples containing cephalomannine, 7-epi-cephalomannine, paclitaxel and other taxanes in different ratios, without significant undesired degradation, for example, of paclitaxel. It is to be understood, however, that these examples are only intended to illustrate some preferred embodiments, and are in no way intended to limit the scope or spirit of the invention as defined in the claims.

EXPERIMENTAL

Raw Materials

Batches of crude plant extracts from *Taxus yunnanensis* or from *Taxus wallachiana* containing approximately 15–40% cephalomannine, approximately 50–70% paclitaxel and approximately 20–35% other taxane/non-taxane components were obtained from the Peoples Republic of China. Chlorine gas was obtained from Matheson Ltd., and Silica gel used was ICN Silitech, 32–63 um, 60 Å, ICN Biomedicals, Inc., Aurora, Ohio. All solvents used were either HPLC or ACS grade and were obtained from Spectrum Chemical Mfg. Corp. Purified water used was deionized in-house.

EXAMPLE 1

Chlorination of Crude Plant Extract in Oxidized Chloroform 1.1 Preparation of Oxidized Chloroform Bromine (3.12 g) was added dropwise to chloroform (4 l) in order to brominate the stabilizer amylene present in the commercially available solvent. The solution was mixed vigorously and left standing at room temperature overnight. The solution was washed once with 1.5% sodium sulfite solution (1.0 l), and then twice with water (2×1.0 l). Hydrogen peroxide solution (3%, 10 ml) was then added, mixed vigorously, and the mixture was allowed to stand for 3–5 days. Chlorine content in the solvent was determined by volumetric analysis. Next, to the solvent sample (5 ml) in a 250 ml Erlenmeyer flask was added 1.0N HCl (10 ml) and water (50 ml). To this mixture was then added KI (2 g), mixed well to dissolve, and the resulting dark brown solution titrated with 0.1N sodium thiosulfate solution. As the color of solution turned light brown, 3–4 drops of starch indicator solution (0.5%, USP) were added. The dark blue—purple solution was further titrated until the solution turned colorless. The volume of sodium thiosulfate solution used to arrive at the end point was noted and chlorine content calculated. The desired chlorine content was in the range of 0.01–0.1%. The solvent was dried with anhydrous sodium sulfate (100 g) and used for the following chlorination reaction.

1.2 Chlorination

Crude plant extract (5.0 g, 28.8% cephalomannine, 62.2% paclitaxel) was dissolved in oxidized chloroform (1 l) in a 3 l flask cooled to 4° C. using an ice bath. HPLC analysis of the mixture after 1 hr showed a paclitaxel to cephalomannine ratio of 8:1. The reaction mixture was stirred at 15° C. for 9 hrs. HPLC analysis of the reaction mixture at this point showed a paclitaxel to cephalomannine ratio 19:1. The reaction mixture was washed with 500 ml water. The pH of the aqueous layer was 2.0. The mixture was then washed with 500 ml 1.0% aqueous sodium sulfite solution, and the pH of the aqueous layer was 7.5. This was followed by two washes with water (2×500 ml).

The pH values of first and second water washes were 7.0 and 6.5 respectively. The combined aqueous layer was reextracted with 150 ml chloroform. The organic layers were combined, dried with anhydrous sodium sulfate (85 g), and evaporated to dryness. The solid residue (5.85 g) was purified by chromatography. LCMS analysis of the chlorinated material indicated formation of dichlorocephalomannine as the product of reaction along with paclitaxel present in the starting material.

1.3 Chromatographic Purification of Chlorinated Material

The chlorinated material (5.85 g) was chromatographically purified using a column (4.1 cm i.d., 62 cm long) packed with silica gel (300 g) by the slurry method using 10% acetone in 1,2-dichloroethane. The sample was dissolved in 10% acetone in 1,2-dichloroethane. Following the first two 700 and 350 ml fractions, all subsequent fractions were limited to 50 ml each. The fractions were analyzed by TLC (TLC-plates were developed with 20% acetone in 1,2-dichloroethane, detected with 1% vanillin in 50/50 sulfuric acid-methanol). Dichlorocephalomannines eluted in fractions 8–13 and yielded 1.6 g solids (~90%) following evaporation of solvents. This material was finally purified by semi-preparative HPLC.

EXAMPLE 2

Chlorination of Crude Plant Extract in 1,2-Dichloroethane 2.1 Preparation of Chlorine Solution in 1,2-Dichoroethane A solution of chlorine in 1,2-dichloroethane was prepared by slow bubbling of chlorine into 1,2-dichloroethane (1 l) precooled to 0°–4° C. using an ice bath. The bubbling was continued for several min. (approx. 10 min.) until the desired concentration of chlorine in 1,2-dichloroethane was achieved. Samples of the solvent were withdrawn periodically and analyzed for dissolved chlorine content as follows: To the solvent sample (5 ml) in a 250 ml Erlenmeyer flask were added 1.0N HCl (10 ml) and water (50 ml). To this mixture was added KI (2 g), mixed well to dissolve, and the dark brown solution was titrated with 0.1N sodium thiosulfate solution. As the color of solution turned light brown, 3–4 drops of starch indicator solution (0.5%, USP) were added. The dark blue—purple solution was further titrated until the solution turned colorless. The volume of sodium thiosulfate solution used to arrive at the end point was noted and chlorine content was calculated. The desired chlorine content was in the range of 0.01–0.1%.

2.2 Chlorination

Crude plant extract (5.0 g) dissolved in 1,2-dichloroethane (200 ml) was added dropwise to the stirred solution of chlorine (0.06%) in 1,2-dichloroethane (1250 ml) cooled to 4° C. by using an ice bath. Following complete addition, the mixture was stirred at 4° C. for 1 hr and a sample was analyzed by HPLC. HPLC analysis indicated that the cephalomannine peak was nearly completely eliminated. The mixture was washed with 1.0% sodium sulfite solution (1.0 l), and water (2×1.0 l). The pH values of the aqueous layers were as follows: sodium sulfite wash, 7.5–8.0; first water wash, 6.0–6.5; second water wash, 5.5. The aqueous layers were extracted with 1,2-dichloroethane (200 ml). The organic layers were combined, dried with anhydrous sodium sulfate (50 g) and evaporated using a rotary evaporator at 40° C. The residual solids were dried in a vacuum oven at 40° C. for 2 hrs to yield 5.3 g chlorinated material. HPLC analysis of this material showed dichlorocephalomannine as the product of the reaction together with paclitaxel present in the starting crude plant extract.

2.3 Separation of Chlorinated Material from Paclitaxel

The chlorinated product mixture from Example 2.2 (5.30 g) was dissolved in acetone (50 ml) in a 250 ml Erlenmeyer flask. To this solution was added hexanes (65 ml), mixed well, and let stand at room temperature until crystallization began to occur. The flask was then stored at 4° C. for 60 hrs. The crystals were filtered, washed with cold 20% acetone in hexanes, and dried in vacuum oven at 40° C. for 3.5 hrs to yield 3.10 g paclitaxel (~95%, crystals I). The combined filtrate and washings were evaporated, and the residual solids dried in a vacuum oven at 40° C. for 2 hrs to yield 1.96 g mother liquor material (mother liquor I). The crystals I (3.10 g) were next dissolved in acetone (32 ml). To this solution was added hexanes (40 ml) and the mixture stored at room temperature for 5 hrs and then at 4° C. overnight. The crystals were filtered, washed with 20% acetone in hexanes, and dried in a vacuum oven at 40° C. for 3 hrs to yield 2.49 g paclitaxel (98.5%, crystals II). The filtrate and washings were combined and evaporated. The residual solids were dried for 2 hrs to yield 0.65 g mother liquor material (mother liquor II). The crystals II (2.49 g) were again dissolved in warm acetone (25 ml). To the solution was added hexanes (25 ml) and the mixture stored at room temperature for 5 hrs and then at 4° C. overnight. The crystals were filtered, washed with 20% acetone in hexanes, and dried in a vacuum oven at 40° C. for 2 hrs to yield 2.01 g paclitaxel (99.5%, crystals III). The filtrate and washings were combined and evaporated. The residual solids were dried in a vacuum oven at 40° C. for 2 hrs to yield 0.47 g mother liquor material (mother liquor III). The mother liquors I, II, and III containing dichlorocephalomannines were then pooled and further separated by semi-preparative HPLC.

2.4 Final Purification of 2"3"-Dichlorocephalomannine Diastereomers

The final purification of dichlorocephalomannine and diastereomers from other impurities was accomplished by semi-preparative HPLC (Waters Deltaprep 3000) using a Waters Deltapak C18 column, 100 Å 19 mm×30 cm with 45% acetonitrile in water as the mobile phase at the flow rate of 15 ml/min. Peak elution was monitored using a UV detector set at 227 nm. Portions of 200 mg material dissolved in methanol (2 ml) were injected. Elution of dichlorocephalomannine diastereomer I (analogue 1) peaked approximately at 86 min. and diastereomer II (analogue 2) at 98 min. Likewise, the dichlorocephalomannine diastereomer III (analogue 3) peaked at approximately 118 min and the corresponding diastereomer IV (analogue 4) peaked at 124 min respectively. Fractions collected from repeated injections were pooled and evaporated at 40° C. under reduced pressure to remove the organic solvent. The crystallized solids were filtered, washed with water, and dried in a vacuum oven at 40° C. to yield pure dichlorocephalomannine and diastereomers. The dichlorocephalomannine diastereomer I isolated in this manner was associated with a contaminant and was repurified by collecting smaller fractions during peak elution following the described HPLC procedure.

The separation and structures of the four diastereomeric dichloro compounds of this invention, (I) (2"R,3"-S)-dichlorocephalomannine (DiCl-I);
(II) (2"S,3"R)-dichlorocephalomannine (DiCl-II);
(III)(2"R,3"R)-dichlorocephalomannine(DiCl-III); and
(IV)(2"S,3"S)-dichlorocephalomannine(DiCl-IV), are set out below in Scheme II.

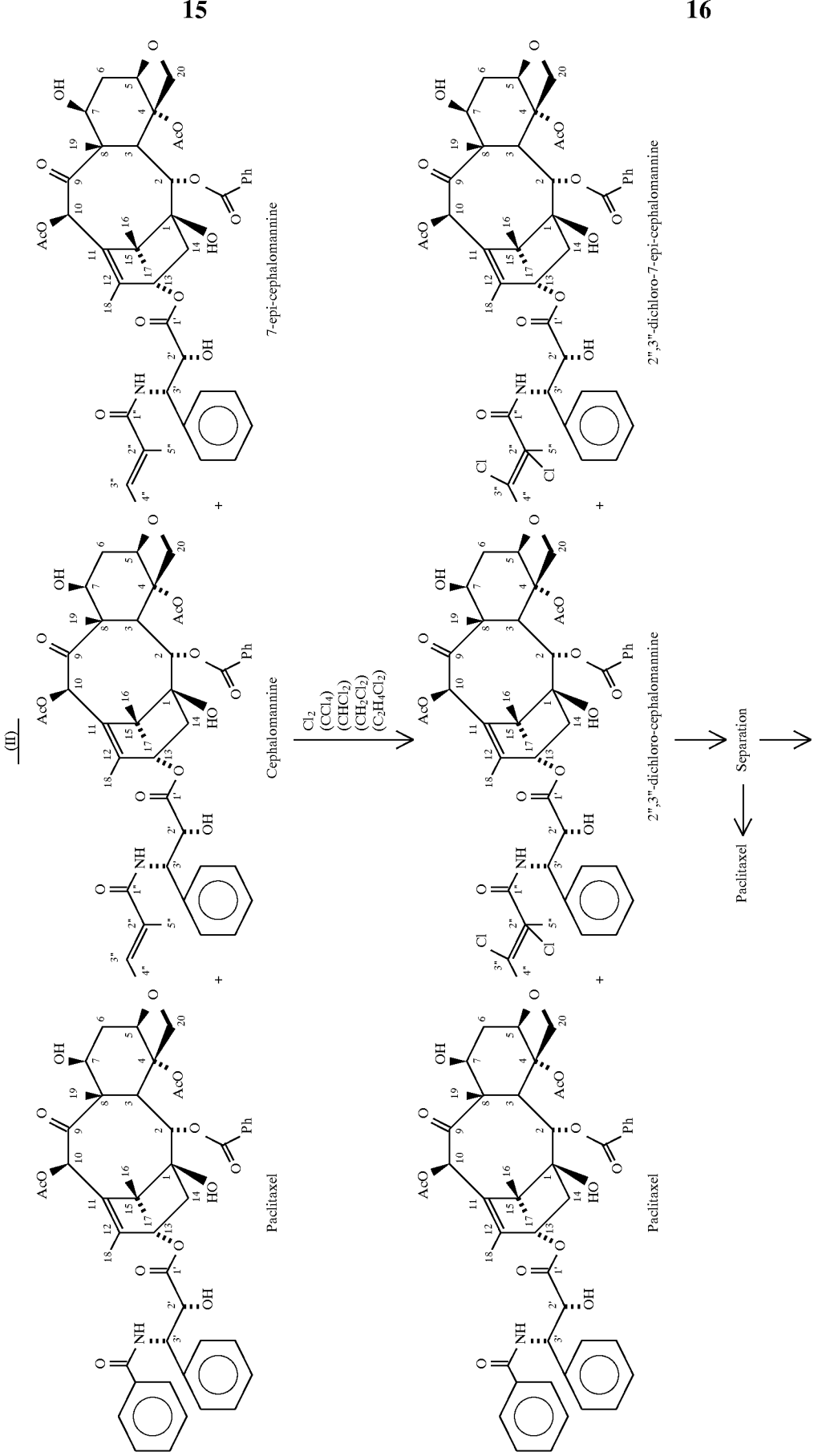

-continued
(II)
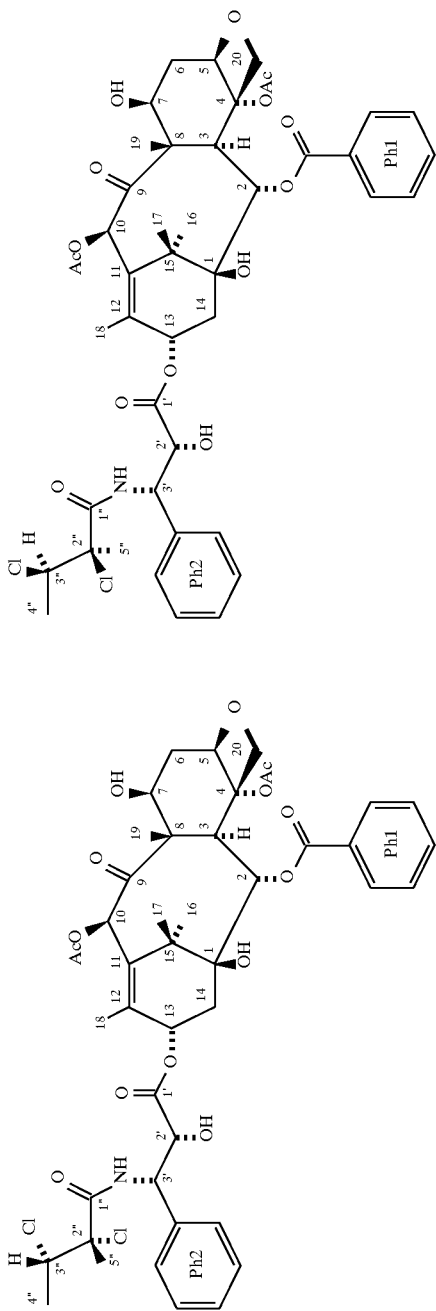
Analogue 1: (2"R,3"S)-Dichlorocephalomannine
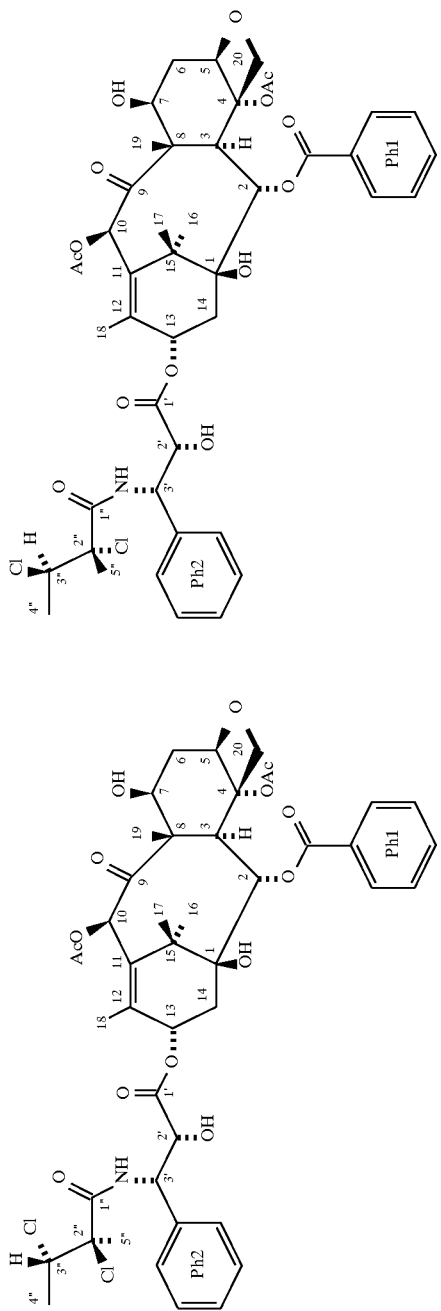
Analogue 2: (2"S,3"R)-Dichlorocephalomannine
Analogue 3: (2"R,3"R)-Dichlorocephalomannine
Analogue 4: (2"S,3"S)-Dichlorocephalomannine
Paclitaxel Analogues (Chlorinated)

Figure 1B:
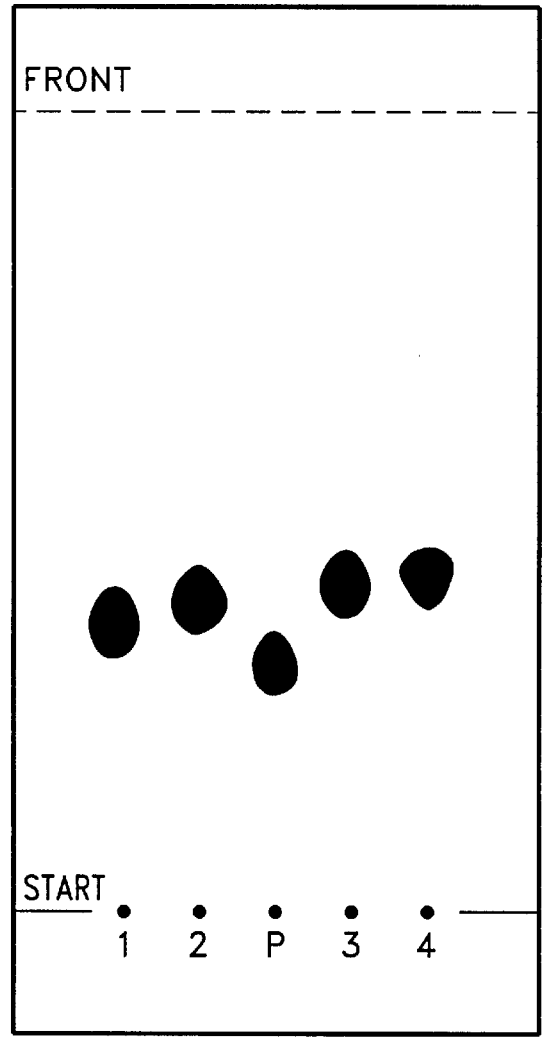

In FIG. 1 a TLC separation of 2",3"-dichlorocephalomannine and (DiCl-I-DiCl-IV) is shown. A key to FIG. 1 is set forth in Table 1.

TABLE 1

| Lane No. | Stereoisomer |
|---|---|
| 1 | DiCl-I |
| 2 | DiCl-II |
| P | Paclitaxel |
| 3 | DiCl-III |
| 4 | DiCl-IV |

| | |
|---|---|
| Plate: | silica gel 60 $F_{254}$ (Merck #5554) |
| Solvent System: | a) 10% $CH_3OH$ in 1,2-dichloroethane |
| | b) hexane/chloroform/EtOAc/$CH_3OH$ 20:60:15:5 |
| Reagent: | a) UV light (254 nm:366 nm) |
| | b) vanilin/$H_2SO_4$ in methanol (50:50 volume) |

Figure 2:
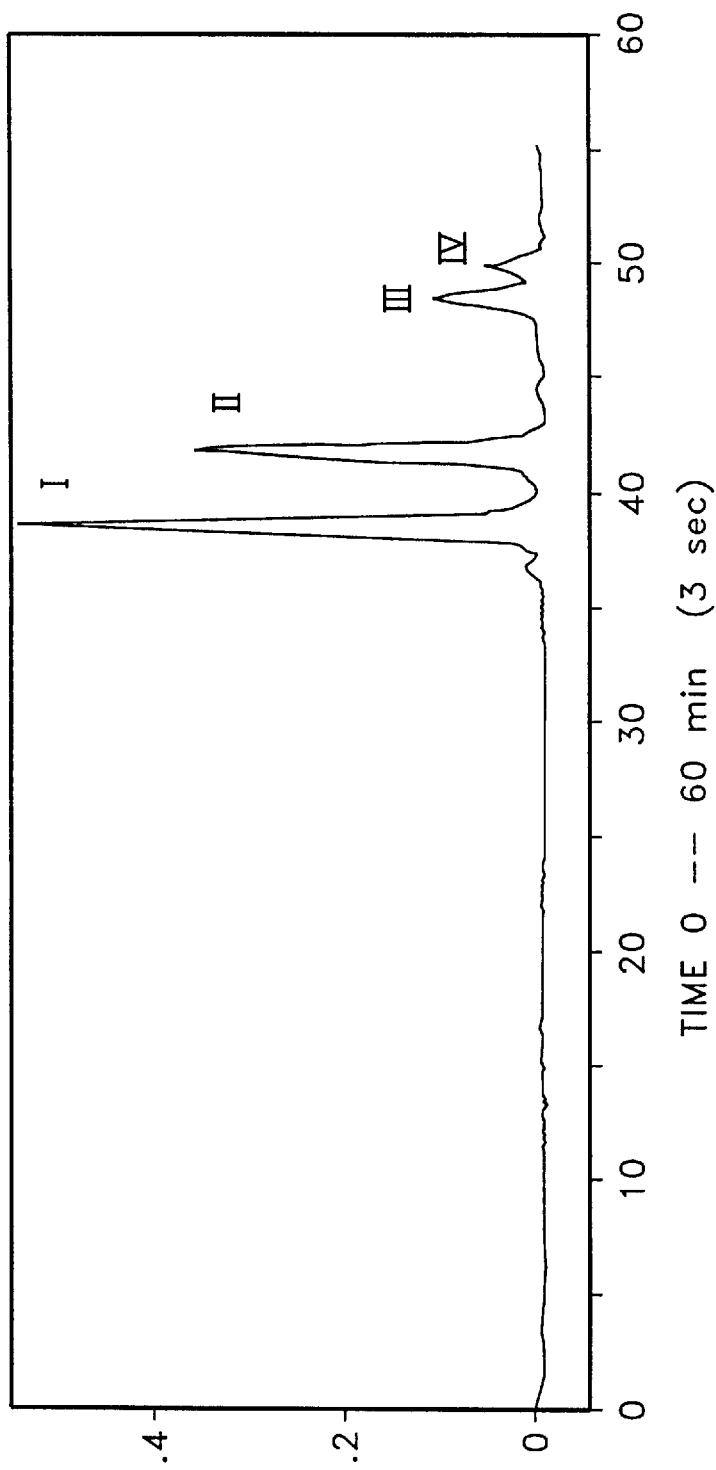
FIG. 2 is an HPLC chromatogram of a mixture of respective dichlorocephalomannine and diastereomers (I, II, III and IV).

FIG. 2 is an HPLC chromatogram of a mixture of the dichlorocephalomannine diastereomers of this invention, with peaks identified below in Table 2.

TABLE 2

| Peak No. | Stereoisomer |
|---|---|
| I | DiCl-I |
| II | DiCl-II |
| III | DiCl-III |
| IV | DiCl-IV |

Figure 3:
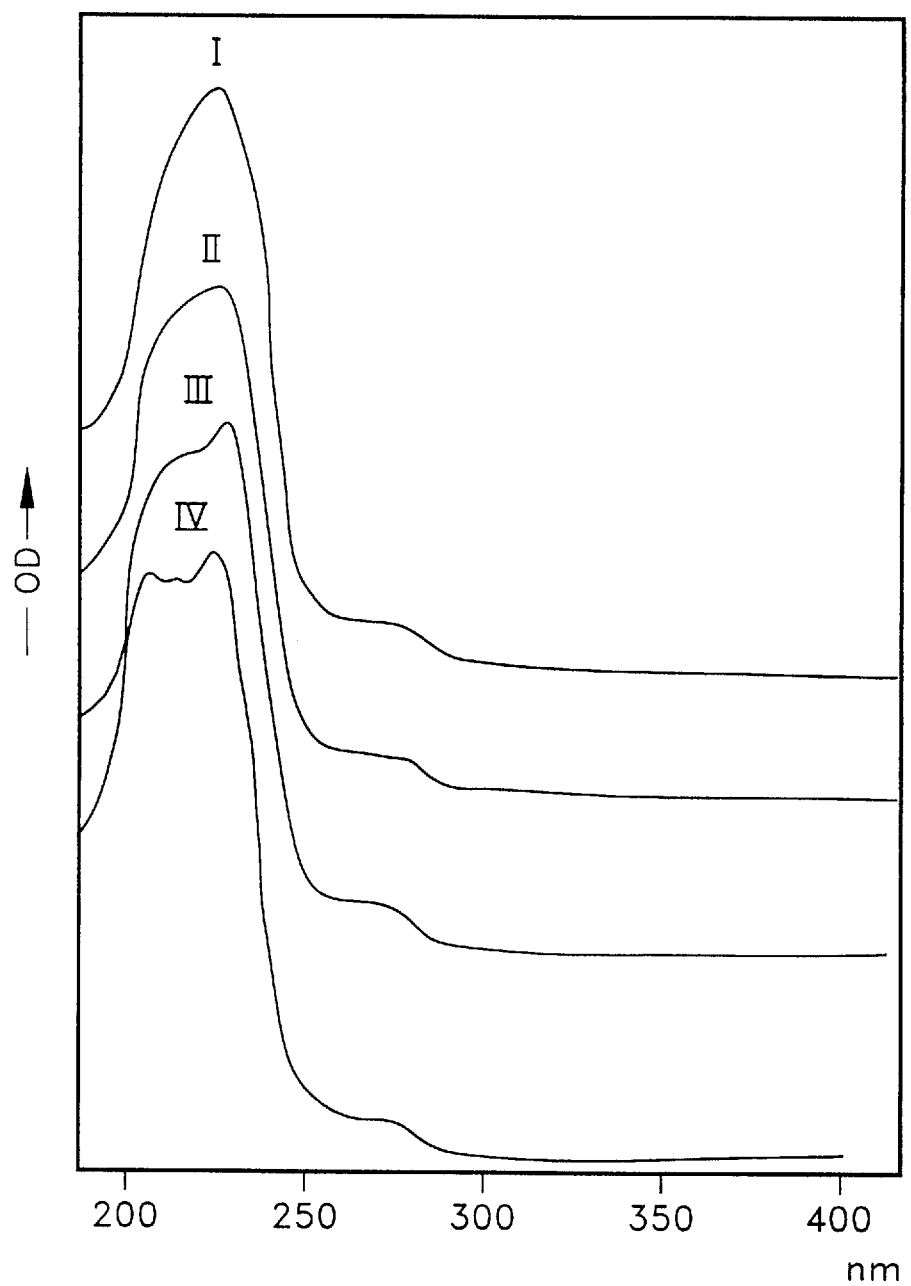
FIG. 3 is a comparison of UV spectra of pure dichlorocephalomannine (I and II), and (2"R,3"R) and (2"S,3"S) dichlorocephalomannine diastereomers (III and IV).

Equipment and conditions employed in generating this chromatogram are as follows:

column: ES Industries, FSP (pentafluorophenyl); 4,6 mm ID× 250 mm; 5 um; 60 Å
solvent system: water/acetonitrile/methanol, 41:39:20
flow rate: 0.50 ml/min.; isocratic
detector: Waters 990 photo diode Array Detector, monitored at 227 nm
injection volume: 20 ul In FIG. 3 there are shown comparative UV spectra of the diastereomers of this invention dissolved in $CH_3OH$. Spectra results are summarized below in Table 3.

TABLE 3

| Peak No. | Stereoisomer | λmax, nm | (ε) |
|---|---|---|---|
| I | DiCl-I | 226.6 | 14813 |
| II | DiCl-II | 227.2 | 14990 |
| III | DiCl-III | 228.2 | 17252 |
| IV | DiCl-IV | 229.4 | 14694 |

Figure 4:
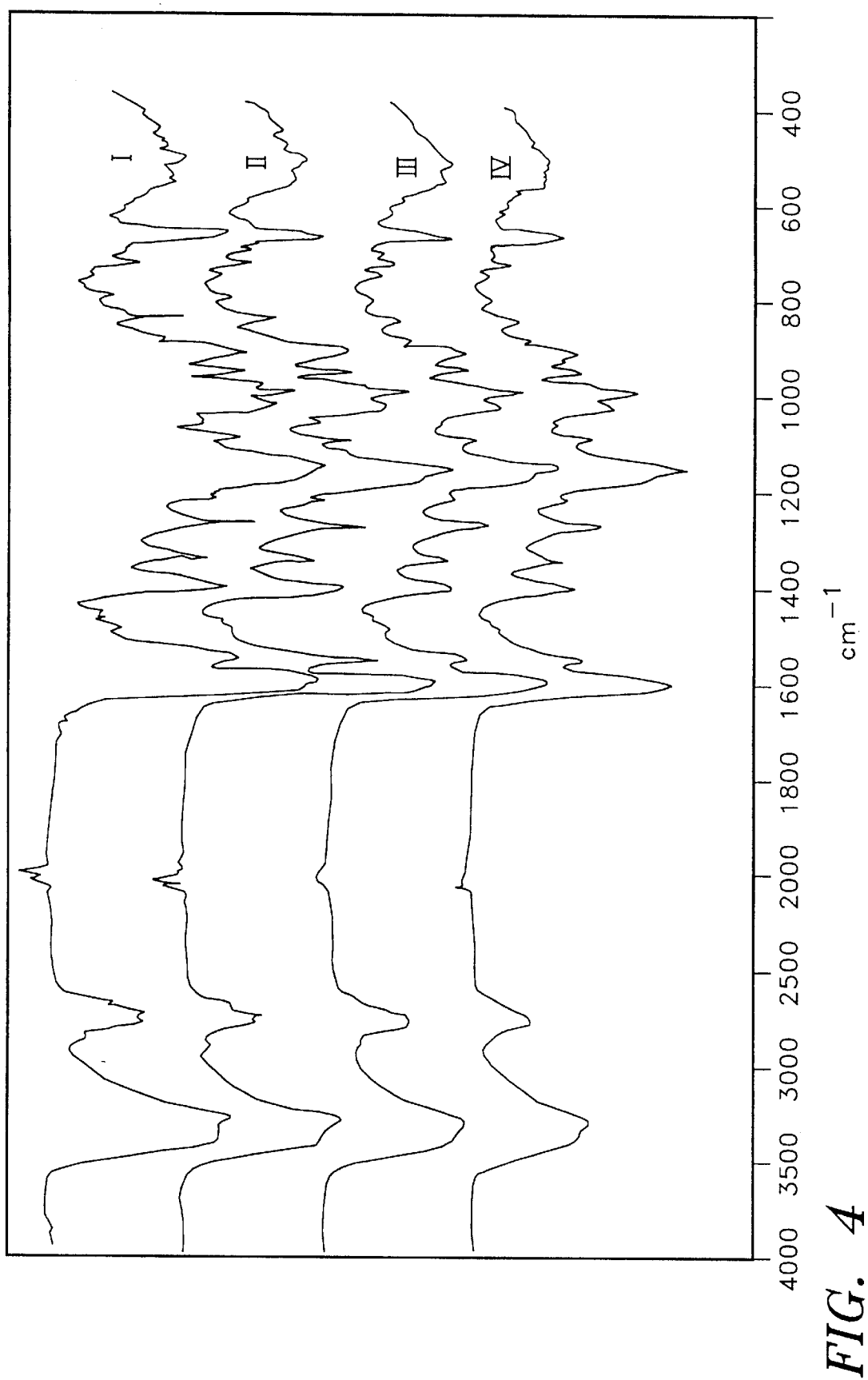
FIG. 4 is a comparison of IR spectra of pure dichlorocephalomannine (I and II) and dichlorocephalomannine diastereomers (III and IV).
Figure 5:
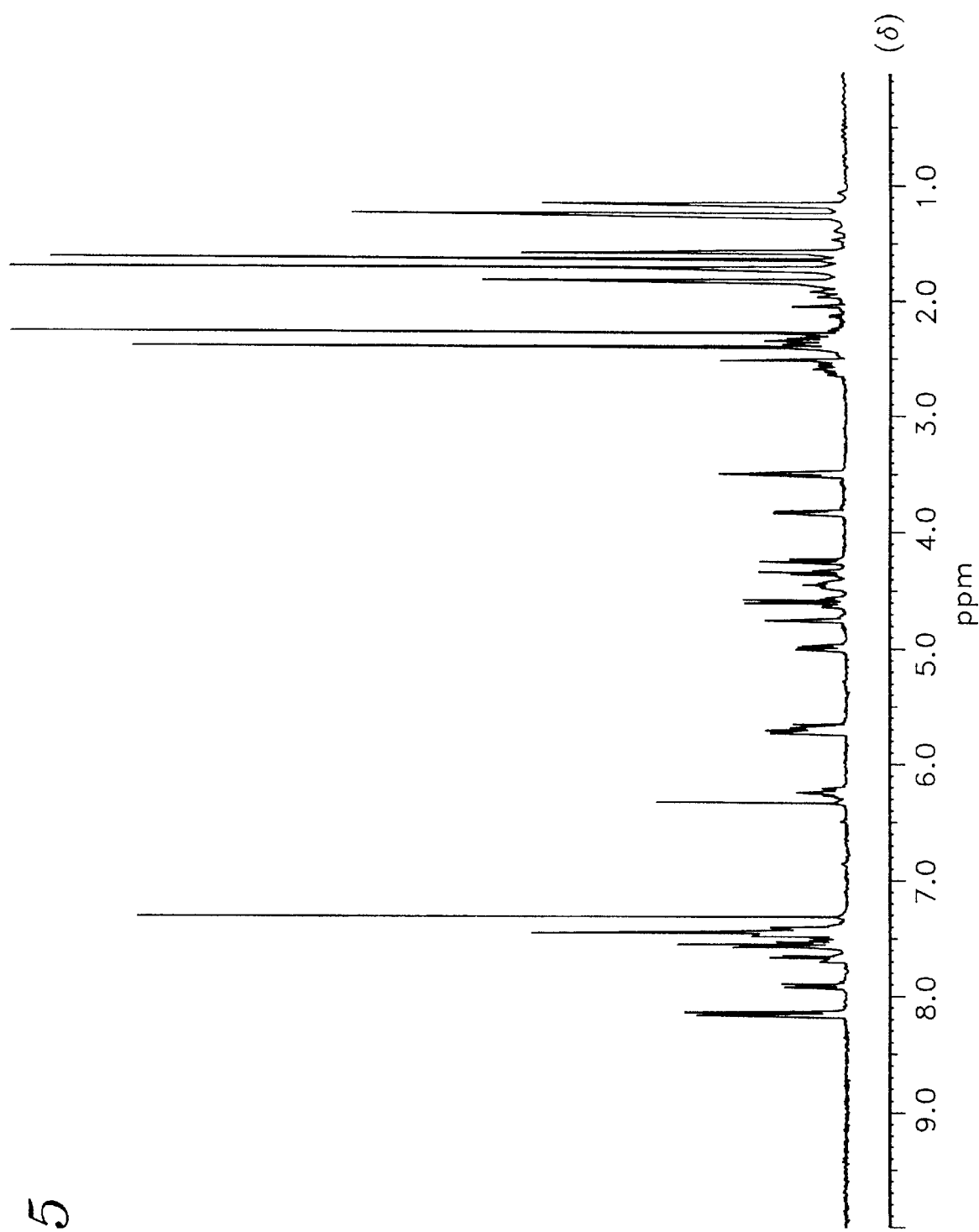
FIG. 5 is $^1$H-NMR spectra of (2"R,3"S) dichlorocephalomannine (I).
Figure 6:
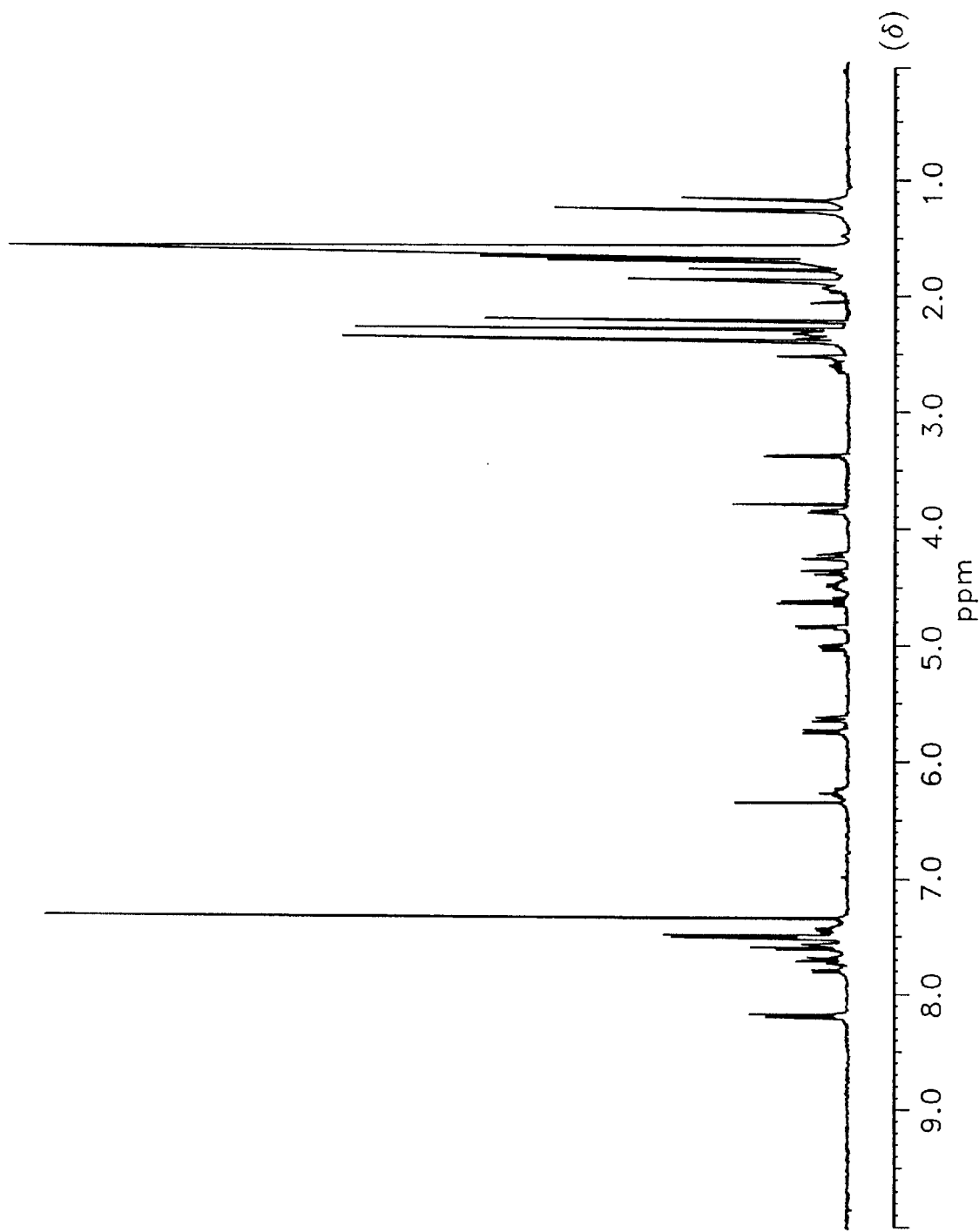
FIG. 6 is $^1$H-NMR spectra of (2"S,3"R) dichlorocephalomannine (II).
Figure 7:
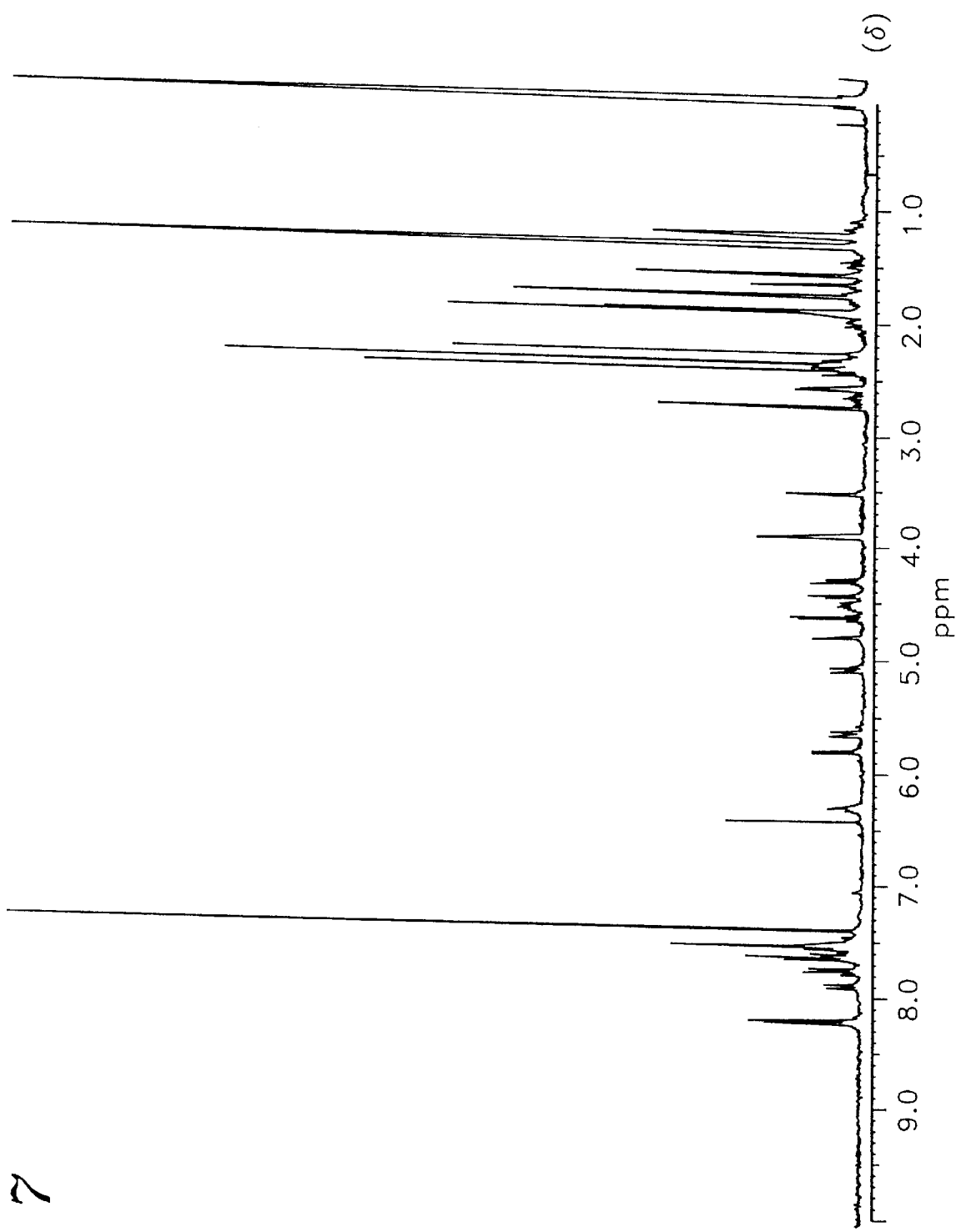
FIG. 7 is $^1$H-NMR spectra of (2"R,3"R) dichlorocephalomannine diastereomer (III).
Figure 8:
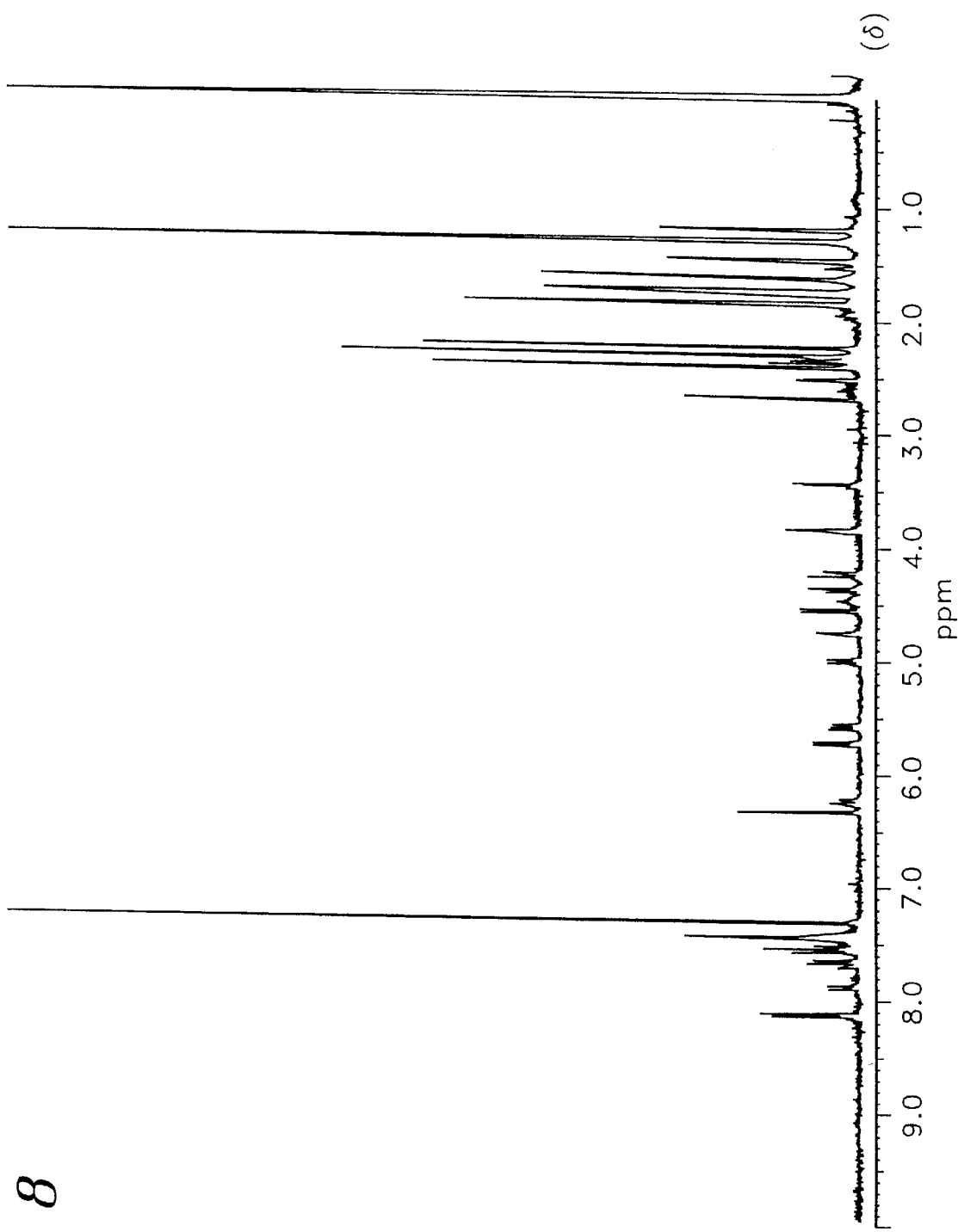
FIG. 8 is $^1$H-NMR spectra of (2"S,3"S) dichlorocephalomannine diastereomer (IV).

FIG. 4 shows comparative of IR spectra of the inventive diastereomers, which are summarized below in Table 4.

TABLE 4

| Band, $cm^{-1}$ | Functional Groups |
|---|---|
| 3500, 1105, 1070 | tert. and sec. OH |
| 3420, 1670, 1580 | —CONH— |
| 3110, 3060, 1605 1505, 770, 710 | mono sub. aromatic rings |
| 2960, 2915, 2870 1465, 1370 | —$CH_3$—; —$CH_2$—; —CH-groups (in alphatic or cyclic compounds) |
| 3020, 1670, 1310 980 | double bonds |
| 1730, 1270 | aromatic esters |

TABLE 4-continued

| Band, $cm^{-1}$ | Functional Groups |
|---|---|
| 1715, 1240 | > = 0 groups |
| 1730, 1180 | acetates |
| 855 | oxetane rings |

Figure 9:
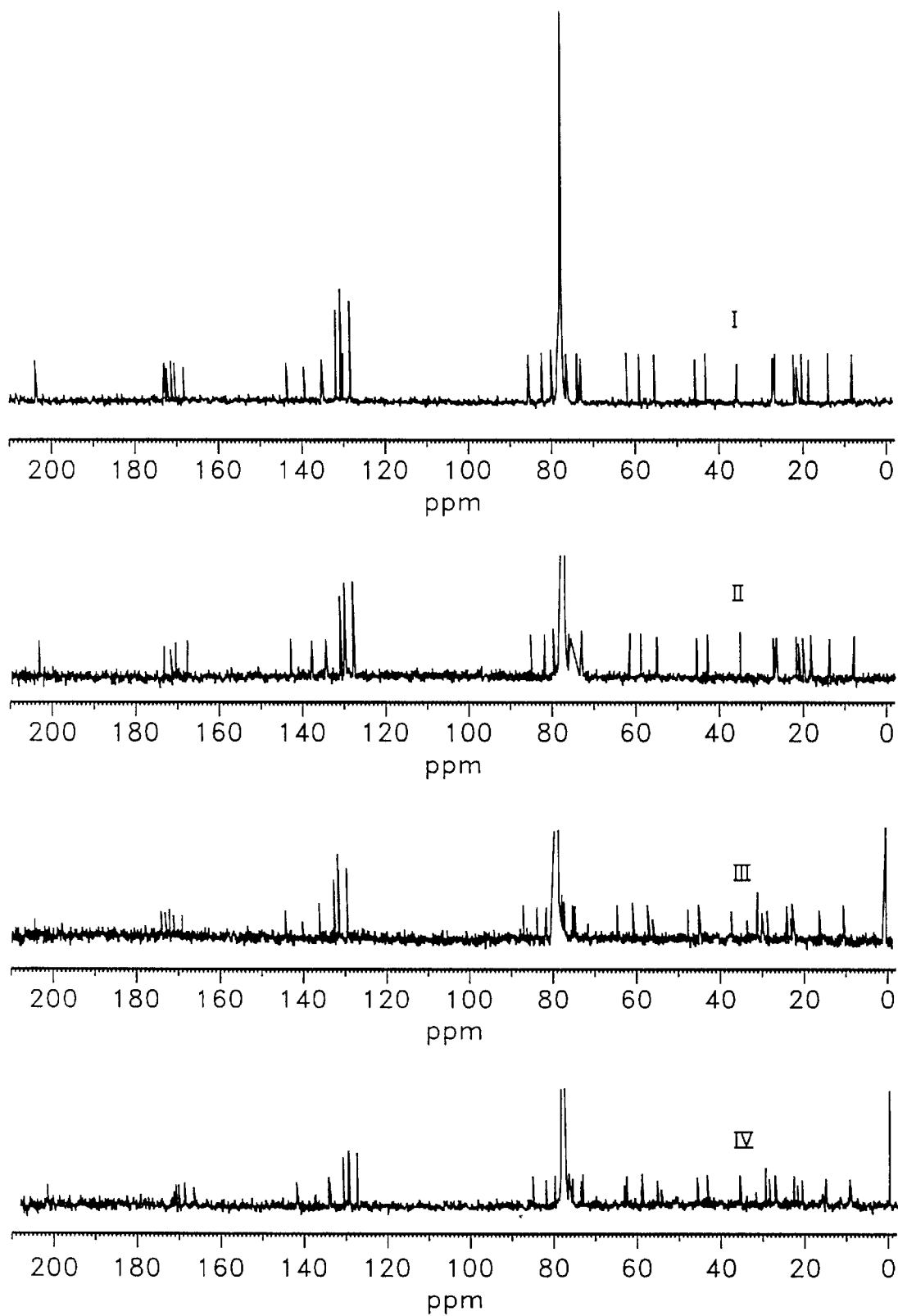
FIG. 9 are comparative of $^{13}$C-NMR spectra of (2"R,3"S) and (2"S,3"R) dichlorocephalomannine (I and II) and (2"R, 3"R) and (2"S,3"S)-dichlorocephalomannine (III and IV) diastereomers respectively.

FIGS. 5–8 are $^1$H-NMR spectra of each of the (2"R,3"S), (2"S,3"R) dichlorocephalomannine and (2"R,3"R),(2"S, 3"S)dichlorocephalomannine diastereomers of the invention, respectively, and FIG. 9 is a comparison of $^{13}$C-NMR (300 MHz) spectra of each of the respective diastereomers, all of which is summarized below as follows.

DICL—I $^1$H-NMR in $CDCL_3$
(300 MHz in ppm; side chain and some important protons only)

| Chemical Shift (ppm) | Assignments |
|---|---|
| 2.54 (m, 1H) | —(H-6a) |
| 1.92 (m, 1H) | —(H-6b) |
| 2.32 (m, 1H) | —(H-14a) |
| 2.32 (m, 1H) | —(H-14b) |
| 4.58 (q6.6, 1H) | —(>CH—Cl—$C_4$") |
| 1.55 (d6.6, 3H) | —(HC—$CH_3$—$C_4$") Cl |
| 1.59 (s, 3H) | (—C—C—$CH_3$—$C_5$") ‖ \| O Cl |

DICL-I $^{13}$C-NMR in $CDCL_3$
(300 MHz in ppm; side chain and some important protons only)

| Chemical Shift (ppm) | Assignments |
|---|---|
| 172.2 | -(C – 1'; C = O) |
| 73.1 | -(C – 2') |
| 55.0 | -(C – 3') |
| 169.3 | -(C – 1') C = O) |
| 61.4 | -(C – 2") |
| 58.7 | -(C – 3") |
| 21.8 | -(C – 4") |
| 27.5 | -(C – 5") |
| 203.6 | -(C – 9; C = O) |

DICL—II $^1$H-NMR in $CDCL_3$
(300 MHz in ppm; side chain and some important protons only)

| Chemical Shift (ppm) | Assignments |
|---|---|
| 2.56 (m, 1H) | —(H-6a) |
| 1.94 (m, 1H) | —(H-6b) |
| 2.34 (m, 1H) | —(H-14a) |
| 2.34 (m, 1H) | —(H-14b) |
| 4.58 (q6.6, 1H) | —(>CH—Cl—$C_3$") |
| 1.55 (d6.6, 3H) | —(HC—$CH_3$—$C_4$") Cl |
| 1.59 (s, 3H) | (—C—C—$CH_3$—$C_5$") ‖ \| O Cl |

DICL-II $^{13}$C-NMR
(300 MHz in ppm; side chain and some important carbons only)

| Chemical Shift (ppm) | Assignments |
|---|---|
| 172.2 | -(C - 1'; C = O) |
| 72.6 | -(C - 2') |
| 55.0 | -(C - 3') |
| 169.9 | -(C - 1") C = O |
| 61.3 | -(C - 2") |
| 58.7 | -(C - 3") |
| 21.8 | -(C - 4") |
| 27.7 | -(C - 5") |
| 203.5 | -(C - 9; C = O) |

DICL—III $^1$H-NMR in CDCL$_3$
(300 MHz in ppm; side chain and some important protons only)

| Chemical Shift (ppm) | Assignments |
|---|---|
| 2.54 (m, 1H) | —(H-6a) |
| 1.90 (m, 1H) | —(H-6b) |
| 2.35 (m, 1H) | —(H-14a) |
| 2.35 (m, 1H) | —(H-14b) |
| 4.50 (qt, 6.6 1H) | —(>CH—Cl—C$_3$") |
| 1.48 (d, 3H) | —(HC—CH$_3$—C$_4$")<br>          \|<br>          Cl |
| 1.52 (s, 3H) | —C—C—CH$_3$—C$_5$")<br>   \|\|  \|<br>   O   Cl |

DICL-III $^{13}$C-NMR
(300 MHz in ppm; side chain and some important carbons only)

| Chemical Shift (ppm) | Assignments |
|---|---|
| 172.2 | -(C - 1'; C = O) |
| 73.0 | -(C - 2') |
| 54.8 | -(C - 3') |
| 169.3 | -(C - 1") C = O |
| 62.7 | -(C - 2") |
| 55.3 | -(C - 3") |
| 21.6 | -(C - 4") |
| 29.3 | -(C - 5") |
| 203.5 | -(C - 9; C = O) |

DICL—IV $^1$H-NMR in CDCL$_3$
(300 MHz in ppm; side chain and some important protons only)

| Chemical Shift (ppm) | Assignments |
|---|---|
| 2.54 (m, 1H) | —(H-6a) |
| 1.90 (m, 1H) | —(H-6b) |
| 2.35 (m, 1H) | —(H-14a) |
| 2.35 (m, 1H) | —(H-14b) |
| 4.50 (q, 6.6 1H) | —(>CH—Cl—C$_3$") |
| 1.48 (d, 6.6 3H) | —(H—C—CH$_3$—C$_4$")<br>          \|<br>          Cl |
| 1.52 (s, 3H) | —C—C—CH$_3$—C$_5$")<br>   \|\|  \|<br>   O   Cl |

DICL-IV $^{13}$C-NMR
(300 MHz in ppm; side chain and some important carbons only)

| Chemical Shift (ppm) | Assignments |
|---|---|
| 172.2 | -(C - 1'; C = O) |
| 72.9 | -(C - 2') |
| 53.9 | -(C - 3') |
| 169.4 | -(C - 1") C = O |
| 62.5 | -(C - 2") |
| 55.0 | -(C - 3") |
| 21.7 | -(C - 4") |
| 29.3 | -(C - 5") |
| 203.5 | -(C - 9; C = O) |

Figure 10:
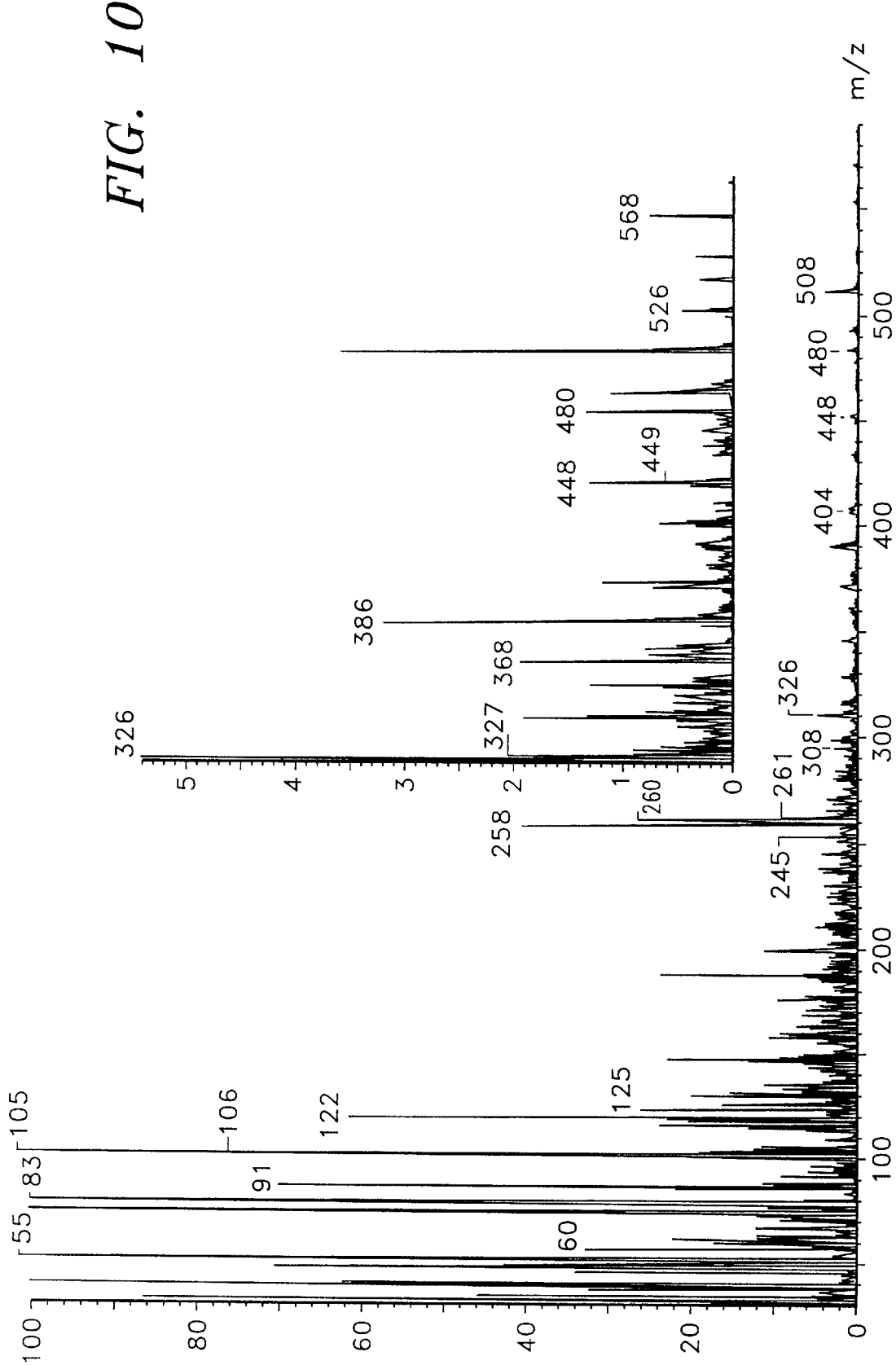
FIG. 10 is a typical EI mass spectrum of (2"S,3"S)-dichloro-7-epi-cephalomannine diastereomer (IV), which is the same fragmentation pattern for all of the diastereomers (I), (II), (III) and (IV).

FIG. 10 is an EI-MS mass spectra of the (2"S,3"S) dichlorocephalomannine diastereomer (IV) which is the same fragmentation pattern for the other diastereomers I, II and III of this invention, and which is summarized below:

EI - MS; [M$^+$] = 902 (m/z, the main fragments)  568 [T]$^+$; 550 [T - H$_2$O]$^+$: 508 [T - AcOH]$^+$; 490 [T - AcOH - H$_2$O]$^+$ 480; 448 [T - 2AcOH]$^+$ or [T - B$_2$OH]$^+$; 386 [T - AcOH - B$_2$OH]$^+$ 326 [T - B$_2$OH - 2AcOH]$^+$; 308 [T-326-H$_2$O]$^+$; 264 [832-T]$^+$; 246 [264-H$_2$O]$^+$; 188; 148; 122 [B$_2$OH]$^+$; 105 [B$_z$]$^+$; 91 [C$_7$H$_7$]$^+$; 83 [C$_4$H$_7$C = O]; 77 [C$_6$H$_5$]; 57; 55; 43

(T = taxane ring, S = acid side chain)

Figure 11:
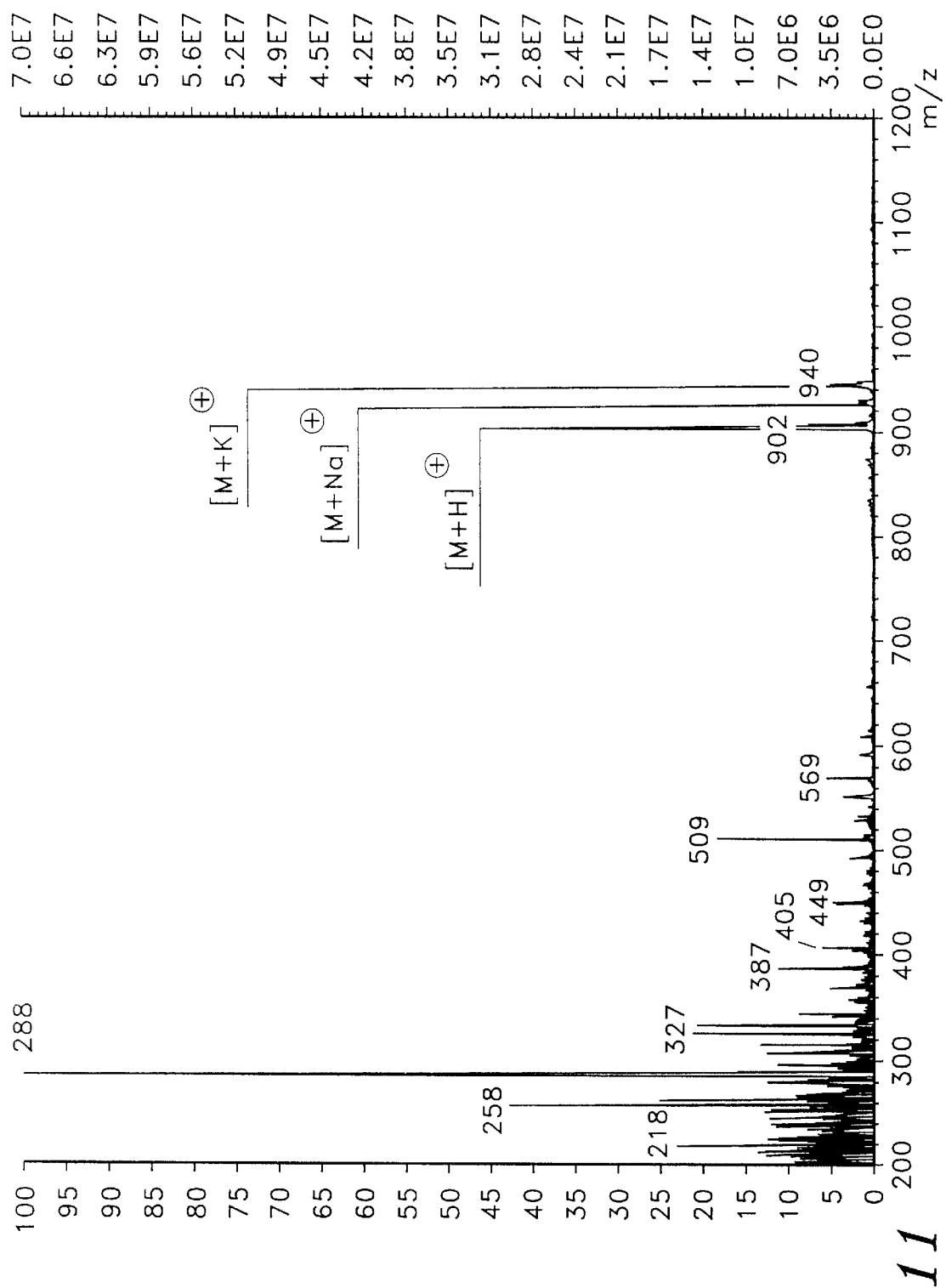
FIG. 11 is a typical FAB+mass spectrum of (2 "S,3"R) dichlorocephalomannine diastereomer (II), which is the same spectrum for all of diastereomers (I), (II), (III) and (IV).
Figure 13C:
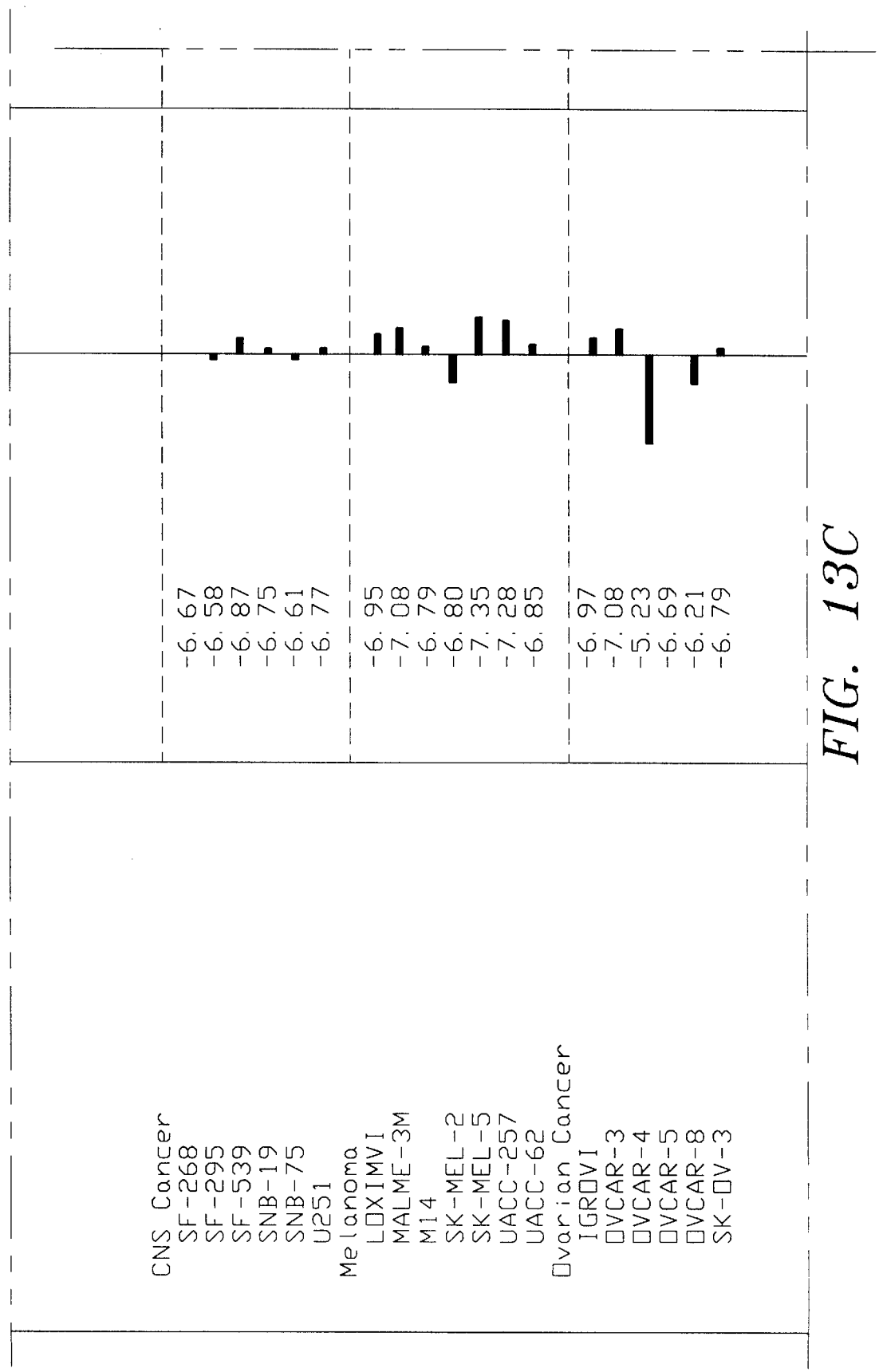
FIG. 13 represents mean graphs of dose response of (2"R, 3"S) -dichlorocephalomannine diastereomer (I) obtained from this invention in a screen of sixty human tumor cell lines.
Figure 13D:
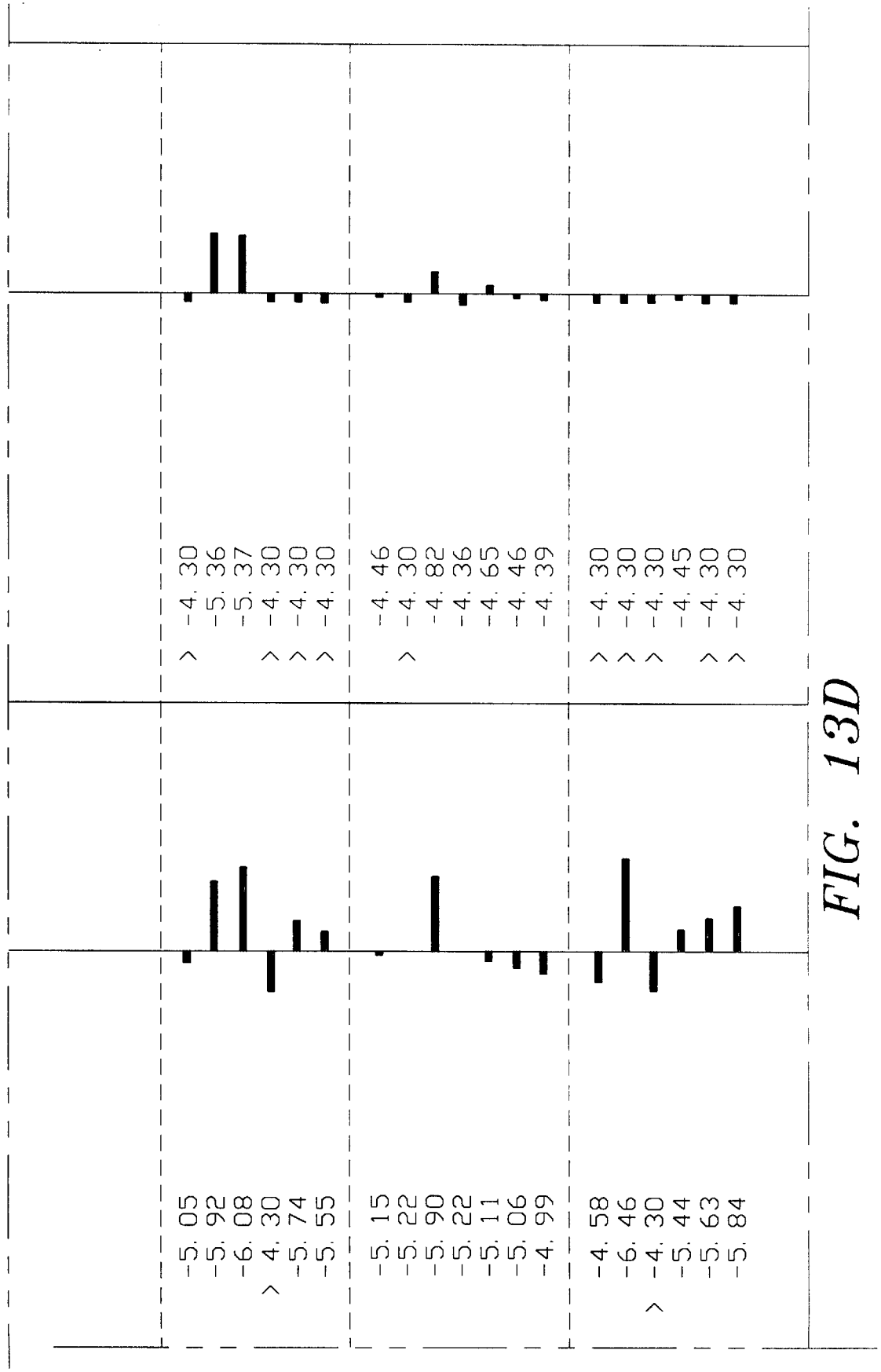
Figure 13E:
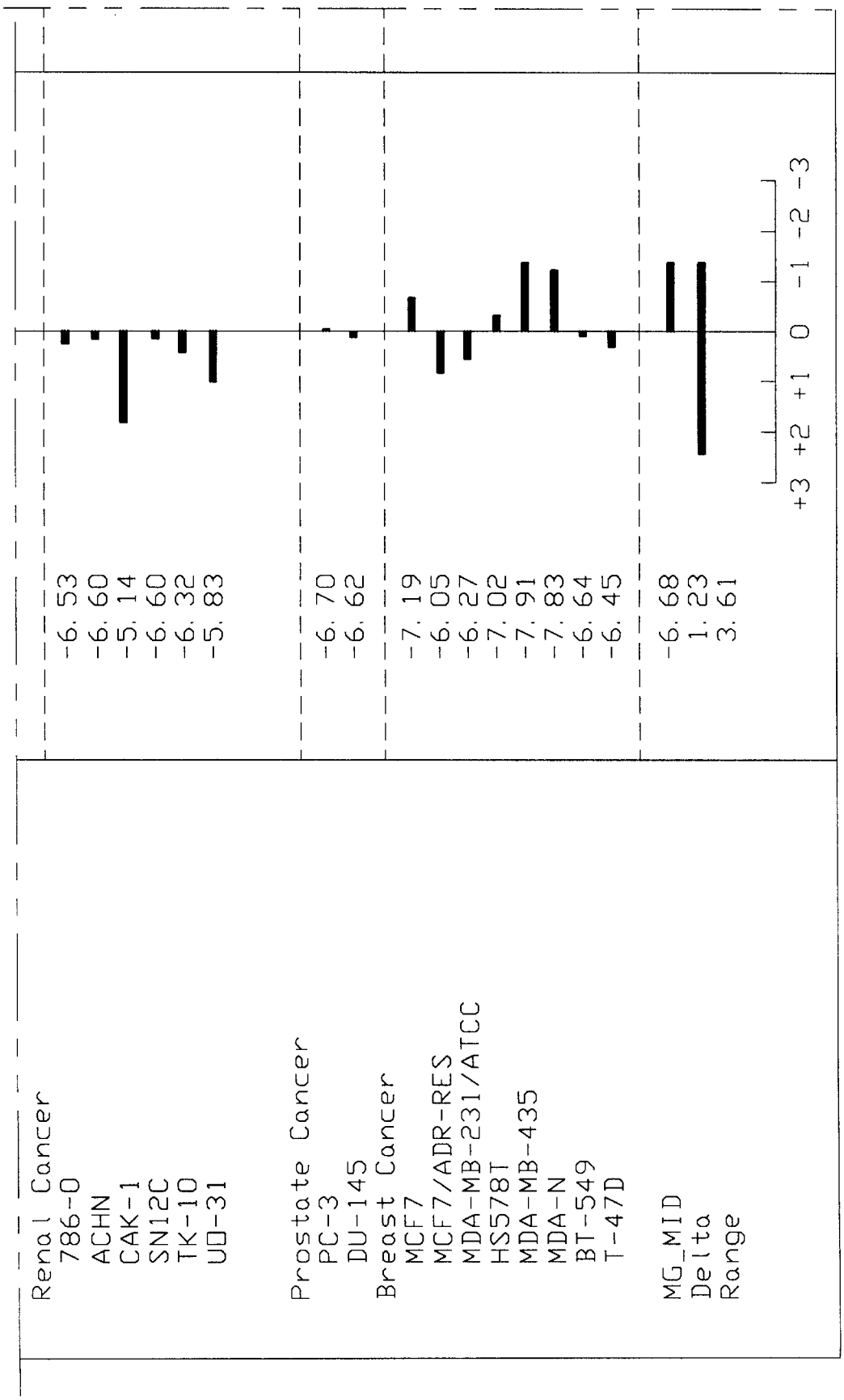
Figure 13F:
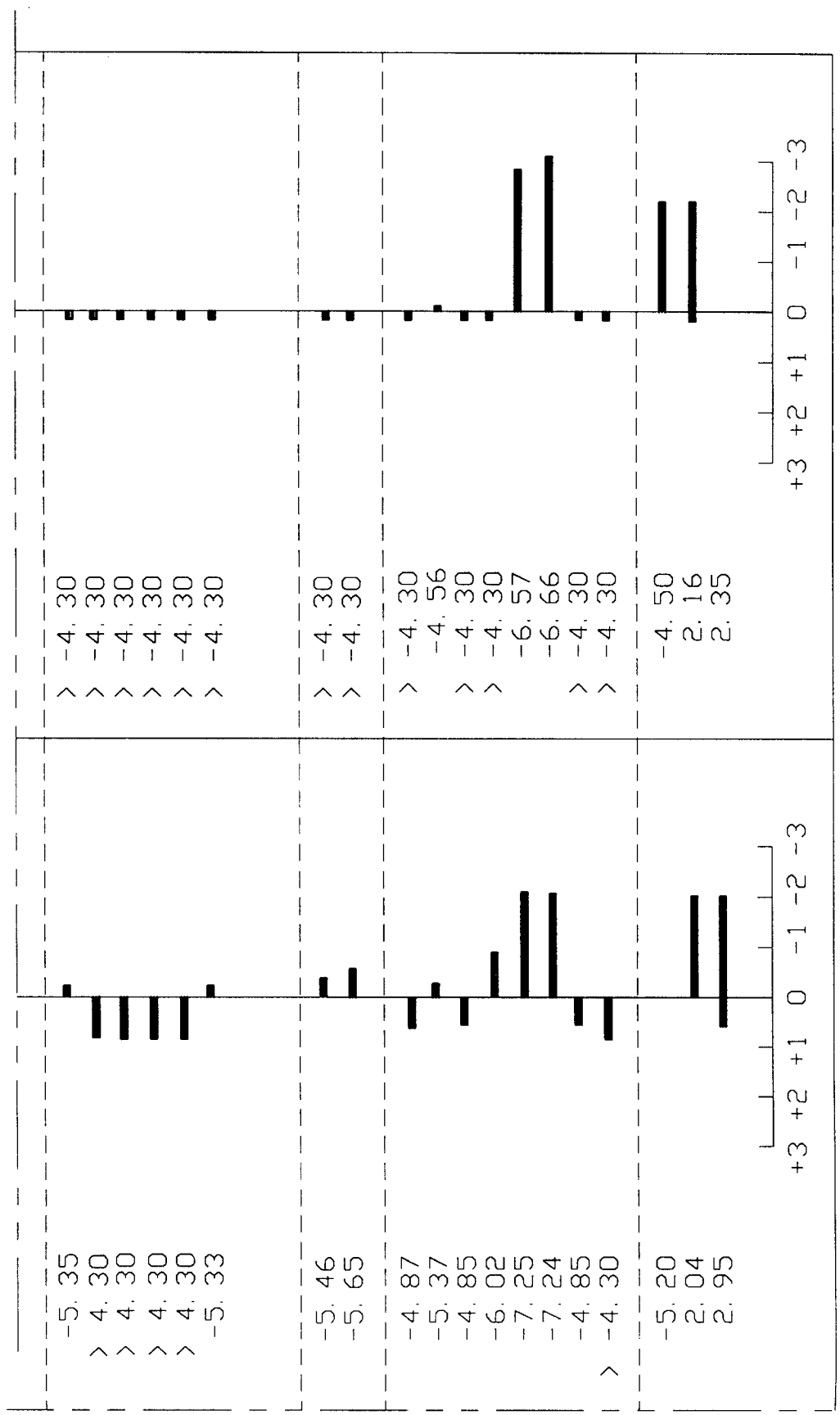
Figure 15A:
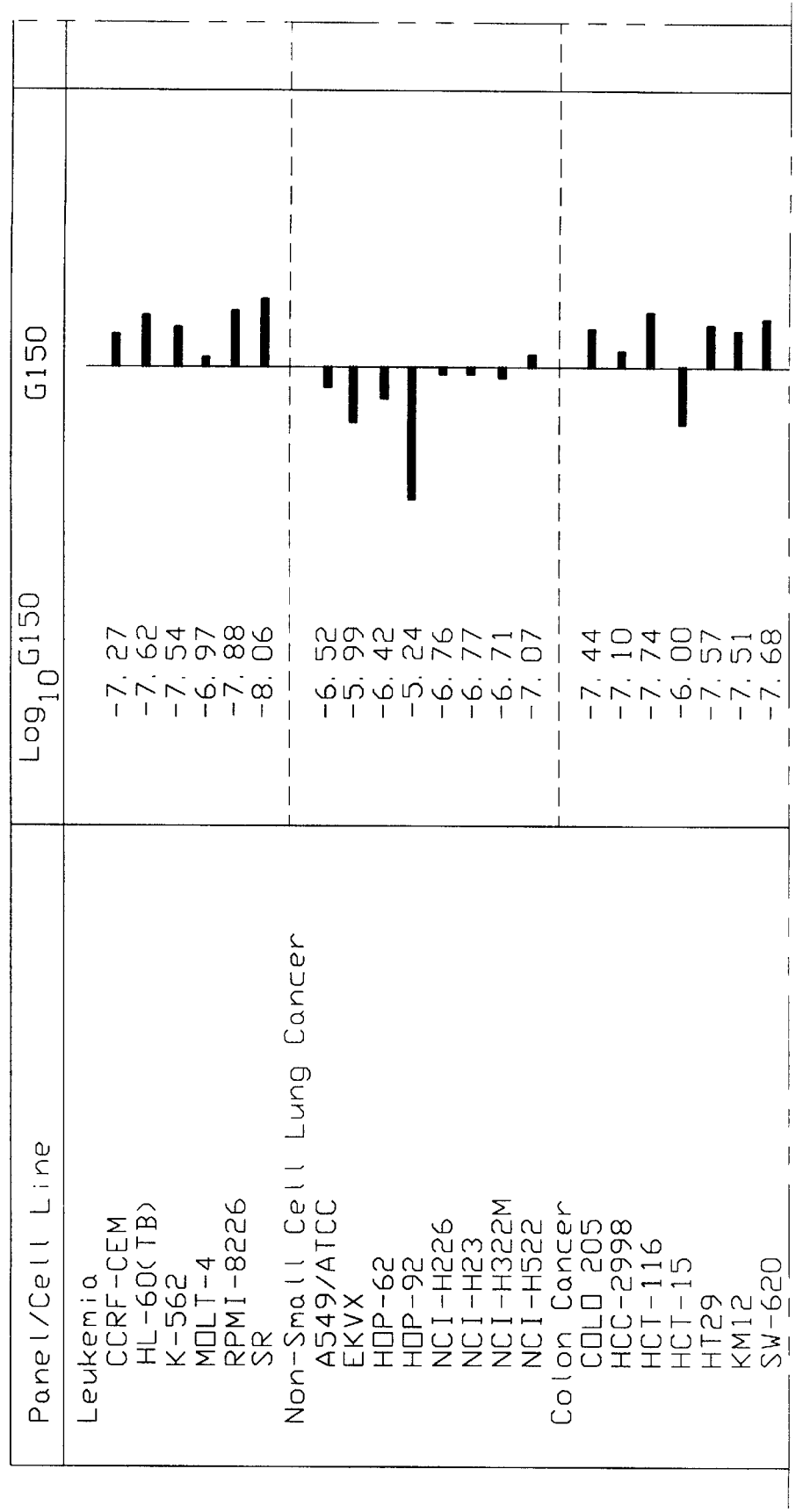
FIG. 15 represents means graphs of dose response of the (2"S,3 "R) -dichlorocephalomannine diastereomer (II) obtained from this invention in a screen of sixty human tumor cell lines.
Figure 15C:
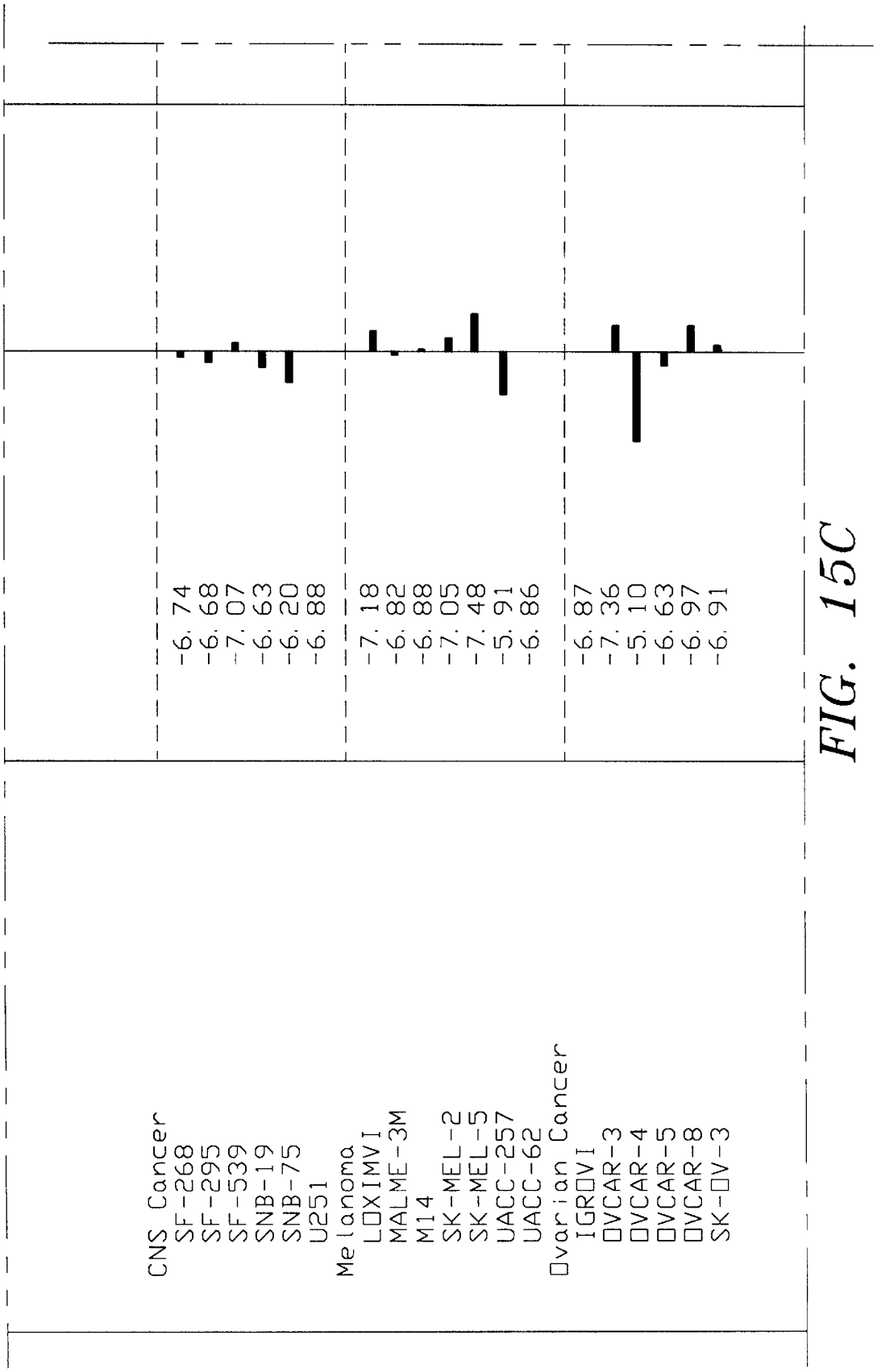
Figure 15D:
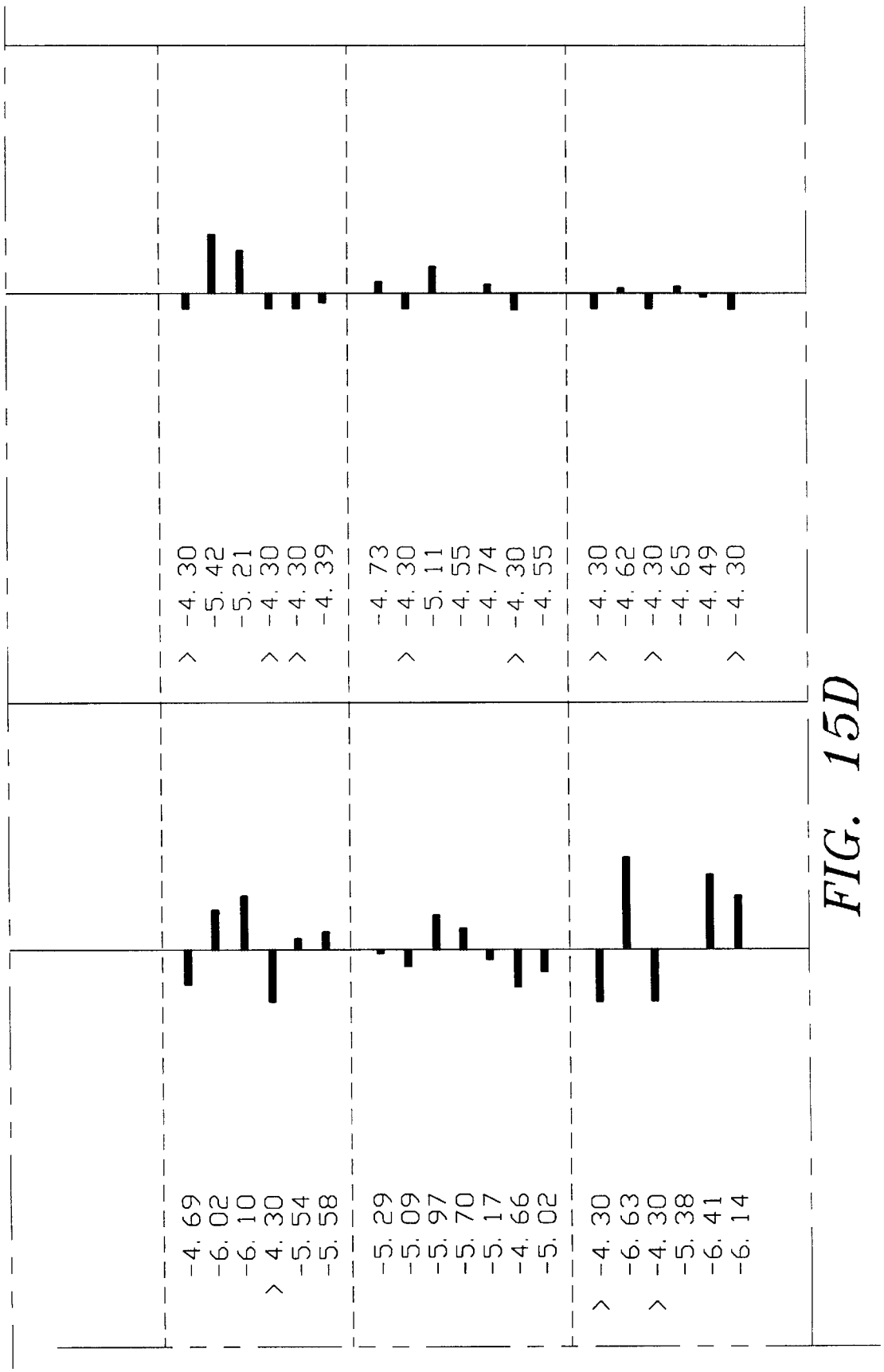
Figure 15E:
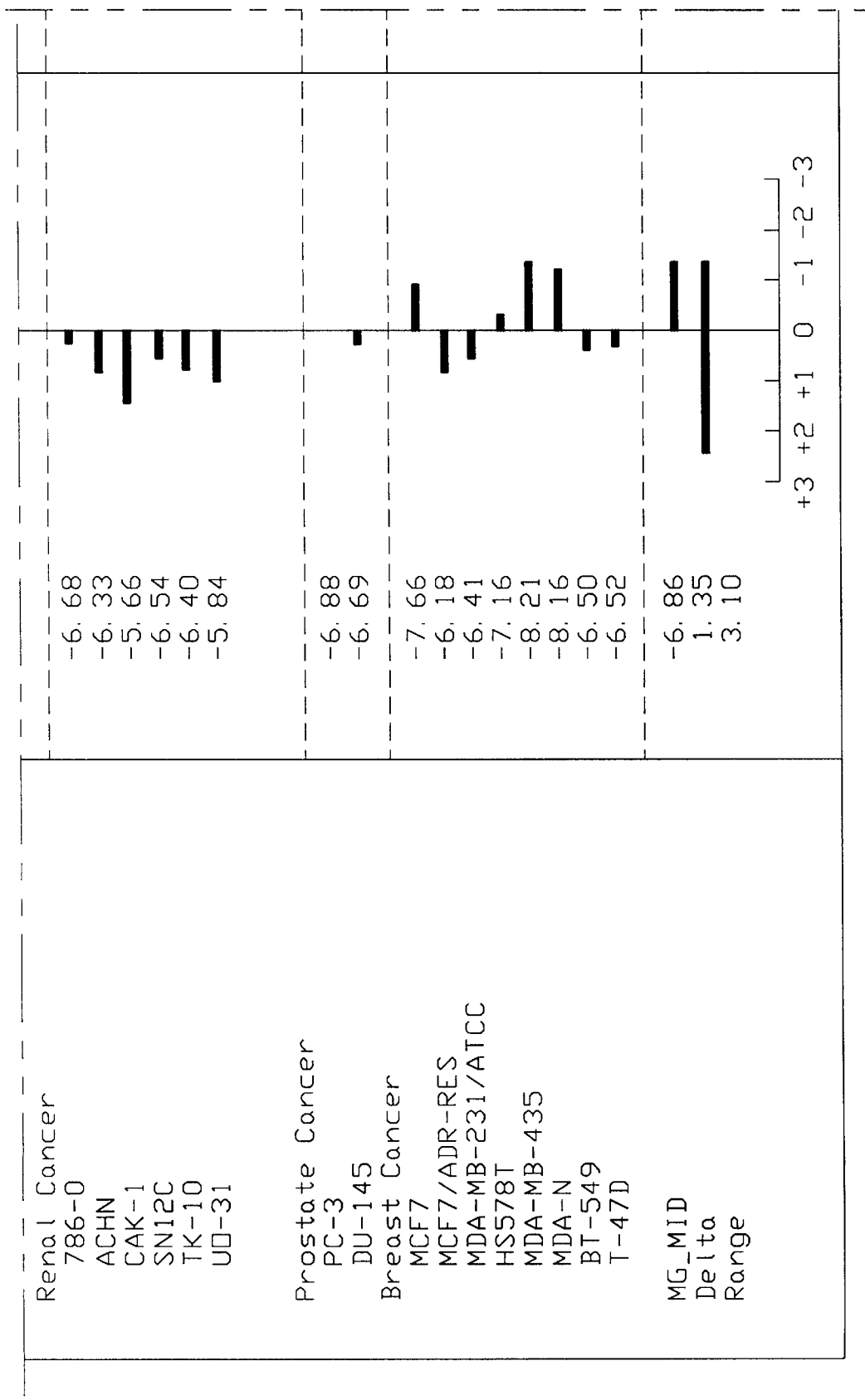
Figure 15F:
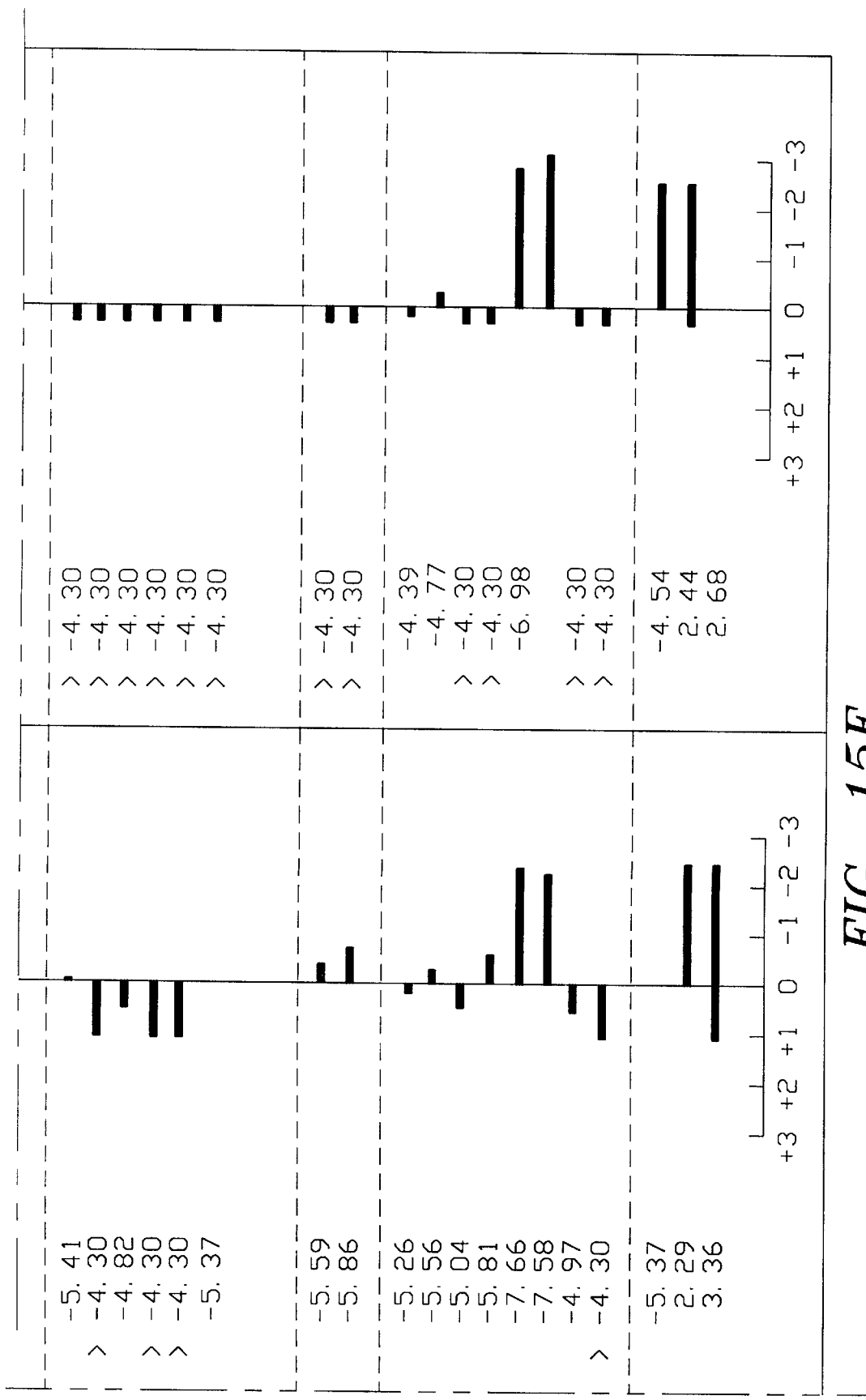

FIG. 11 is FAB$^+$spectrum of the (2"S, 3"R) dichlorocephalomannine diostereomer (II), of this invention, which is representative of all the inventive diastereomers I, II, III and IV, and which is summarized below.

940 ([M + K]$^+$); 924 ([M + Na]$^+$); 902 ([M + H]$^+$); 842 ([M-60$^+$]; 832 ([cephal]); 824 ([M-60-18]$^+$); 569 ([T]$^+$; 551 ([T-18]$^+$); 527 ([T-43]$^+$); 509 ([T-60]$^+$); 491 ([T-60-18]$^+$); 449/448 ([T-122]$^+$); 405 ([S-18]); 387 ([T-60-122]$^+$); 327 ([387-60]$^+$); 309 ([327-18]$^+$); 264 ([832-T]$^+$); 246 ([264-18]$^+$); 218 ([264-46]$^+$); 105 ([C$_6$H$_5$CO]$^+$); 91 ([C$_7$H$_7$]$^+$); 77 ([C$_6$H$_5$]$^+$);

(T = taxane ring; S = acid side chain)

Physico-chemical properties of the inventive dichlorocephalomannine/dichloro-7-epi-cephalomannine diastereomers are summarized below in Table 5.

TABLE 5

Physico-Chemical Properties of Chloro-Analogues of Paclitaxel

| Property | DiCl-I | Di-Cl-II | DiCl-III | DiCl-IV |
|---|---|---|---|---|
| Appearance | White to off-white crystals | White to off-white crystals | White to off-white crystals | White to off-white crystals |
| Melting point | 190–192° C. | 186–188° C. | 178–182° C. | 160–162° C. |
| Molecular formula | $C_{45}H_{53}O_{14}NCl_2$ | $C_{45}H_{53}O_{14}NCl_2$ | $C_{45}H_{53}O_{14}NCl_2$ | $C_{45}H_{53}O_{14}NCl_2$ |
| Molecular weight | 902.8 | 902.8 | 902.8 | 902.8 |
| $[\alpha]22.5_D$ | −56.9° | −45.9° | −38.8° | 40.2 |
| IR* (cm$^{-1}$) | 3500, 1105, 1070; 2960, 2915, 2870, 1240; 1730, 1180; | 3420, 1670, 1580; 1465, 1370; 3020, 855; 760 | 3110, 3060, 1605, 1670, 1310, 980; | 1505, 770, 710; 1730, 1270; 1715, |
| UV $\lambda_{max}$; ($\epsilon$) | 226.6 nm; 14813 | 227.2 nm; 14990 | 228.2 nm; 17252 | 229.4 nm; 14694 |
| TLC** ($R_f$) solvents: | | | | |
| A: | 0.41 | 0.43 | 0.46 | 0.49 |
| B: | 0.33 | 0.36 | 0.39 | 0.44 |
| HPLC*** (RT) | | | | |
| condition 1: | 38.50 min. | 41.75 min. | 48.29 min. | 49.74 min. |
| condition 2: | 37.75 min. | 41.83 min. | 45.98 | 48.01 min. |

\* The IR spectra of DiCl-I–IV are superimposable.

\*\*
Solvent System A: Methanol-1,2,-Dichloroethane- (1:9).
Solvent System B: Hexane-Chloroform-Ethylacetate-Methanol-(2:6:1.5:0.5)

\*\*\*
Condition 1: Column: ES Industries FSP (Pentafluorophenyl) 4.6 mm ID × 250 mm, 5 µm particle size, 60Å pore size; mobile phase - water - acetonitrile - methanol - (41:39:20); flow rate 0.50 ml/min; separation mode - isocratic; detector - Waters 990 Photodiode Array Detector; elution monitored at 227 nm; injection volume - 20 µl.
Condition 2: Column: Phenomenex 4.6 mm ID × 250 mm, 5 µm particle size, 80Å pore size; mobile phase - water - acetonitrile - methanol - (45:40:15); flow rate - 0.50 ml/min; separation mode - isocratic; detector - Waters 490 programmable multiwavelength detector, elution monitored at 227 nm; injection volume - 80 µl total mixture.

EXAMPLE 3

In Vitro Studies showing Antitumor Efficacy of (2"R,3"S)-DichloroCephalomannine and (2"S,3"R)-Dichlorocephalomannine.

As is known, paclitaxel (such as, for example, Taxol®-Bristol-Myers Squibb) and its derivative Taxotere® (Rhône-Poulenc) exhibit highly desirable antitumor efficacy against a number of tumors. These antineoplastic drugs act in a unique manner by preventing depolymerization of tubulin forming microtubules of the mitotic spindle which is essential for cell division, and thus cause cell division to cease along with tumor cell proliferation. The mechanism of action of paclitaxel, its pharmacology etc. is described, for example, in Rowinsky et al. taxol: A novel investigational antimicrotuble agent, J. Natl. Cancer Inst., 82:1247 (1990).

In accordance with this invention, isolated and purified diastereomers of dichlorinated cephalomannine, (2"R,3"S)-dichlorocephalomannine and (2"S,3"R)-dichlorocephalomannine, have been found to exhibit strong paclitaxel-like antitumor efficacy in vitro, thereby providing a valuable addition to known antitumor therapeutic agents and an important alternative to paclitaxel and its derivatives, such as Taxotere.

The following in vitro studies conducted by the National Cancer Institute's Developmental Therapeutics Program demonstrate the strong antitumor efficacy of the inventive dichlorocephalomannine diastereomers.

The Developmental Therapeutics Program provides as a service to the public an in vitro anticancer drug discovery screen using a panel of sixty different human tumor cell lines over which candidate drugs are tested at defined ranges of concentrations. See Boyd et al., Drug Development Research 34:91–109 (1995), the entirety of which is incorporated herein by reference. As discussed in Boyd et al., the screen is designed and operated in such a manner that both relative and absolute sensitivities of each of the cell lines comprising the screen are reproducible to the degree that a characteristic profile ("fingerprint") of a respective cell lines' response to a drug candidate can be generated. Recent studies of the in vivo counterpart of the NCI in vitro screen have indicated the in vitro screen to be an effective selector of compounds with in vivo anticancer efficacy. See Grever et al., Proc. Am. Assoc. Cancer Res. 35:369 (1994).

Operation and interpretation of the screen are discussed in detail in Boyd et al., as well as in several other articles cited therein and thus need not be repeated here. In vitro antitumor efficacy of the respective dichlorocephalomannine diastereomers is shown in FIGS. 12 and 13 (DiCl-I); and, 14 and 15 (DiCl-II), Testing Results and Mean Graphs, respectively.

Discussion of Results

In the NCI in vitro anticancer drug screen, the effect of an antitumor candidate, i.e. 2", 3" -dichlorocephalomannine diastereomers of the present invention, on a cell line, percentage growth (PG), and calculated response parameters are discussed in detail in Boyd et al., Data display and analysis strategies for the NCI-disease-oriented in vitro antitumor drug Screen, Cytotoxic Anticancer Drugs: Models and Concepts for Drug Discovery and Development, Kluwer Academic Publishers, Amsterdam, pp. 11–34 (1992), and Monks et al. *Feasibility of a high-flux anticancer drug screen utilizing a diverse panel of human tumor cell lines in culture*, J. Natl. Cancer Inst. 83:757–766 (1991), the entire disclosures of which are incorporated herein by reference. In general, in the screening data reports, FIGS. 12 and 14, and mean graphs, FIGS. 13 and 15, "$GI_{50}$" represents the 50% growth inhibition factor, "TGI" represents a total growth inhibition, or cytostatic level of effect, and "$LC_{50}$" represents a lethal concentration, or net cell killing or cytotoxicity parameter. Values accompanied by a "<" signify that the dosage level or real value is a value that is something less than the lowest tested concentration, and values accompanied by a ">" sign indicate that the effective dosage or real value is a level greater than the highest tested concentration.

The mean graphs are obtained from $GI_{50}$, TGI and $LC_{50}$ concentrations obtained for compounds tested against each cell line in the NCI in vitro screen. A detailed discussion of mean graph construction is provided in Boyd et al. (1995). In interpreting the mean graphs in general, a bar projecting to the right represents sensitivity of a particular cell line to an anticancer candidate in excess of the average sensitivity of all tested cell lines, while bars extending to the left represent cell lines which are less sensitive on average to the anticancer candidate. As the bar scales are logarithmic, a bar which extends, for example, 2 or 3 units to the right of the vertical reference line in, say a $GI_{50}$ mean graph, indicates that the anticancer candidate achieved a response parameter for a particular cell line at a concentration one- hundredth to one-thousandth of the mean concentration required over all cell lines, therefore indicating that the particular tumor cell line is unusually sensitive to the tested candidate.

We claim:

1. A compound of the formula,

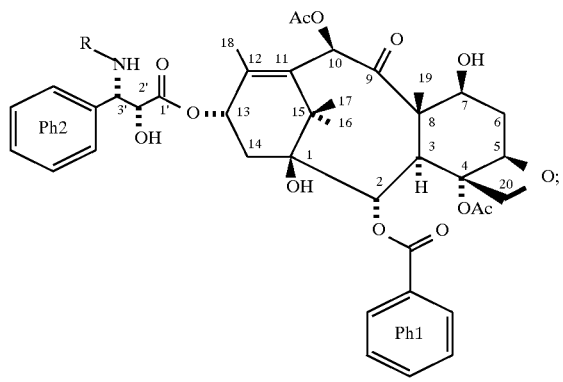

wherein R is selected from the group consisting of:

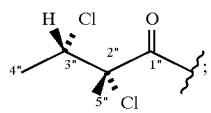 (I)

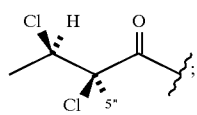 (II)

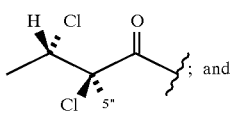 ; and (III)

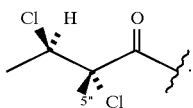 . (IV)

2. A pharmaceutical formulation which comprises as an active ingredient one or more of the compounds of claim 1 or a pharmaceutically acceptable salt thereof associated with one or more pharmaceutically acceptable carriers, excipients or diluents thereof.

3. A method of treating animal and human tumors which comprises administering to an animal or human in need thereof a tumor sensitive amount of one or more of the compounds of claim 1.

4. The method of claim 3 wherein, in the compound administered,

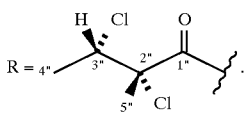

5. The method of claim 3 wherein, in the compound administered,

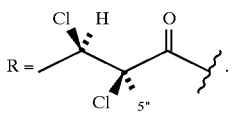

6. The method of claim 3 wherein, in the compound administered,

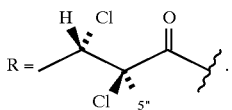

7. The method of claim 3 wherein, in the compound administered,

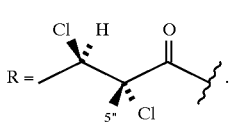

8. A method for the production of a compound of the formula,

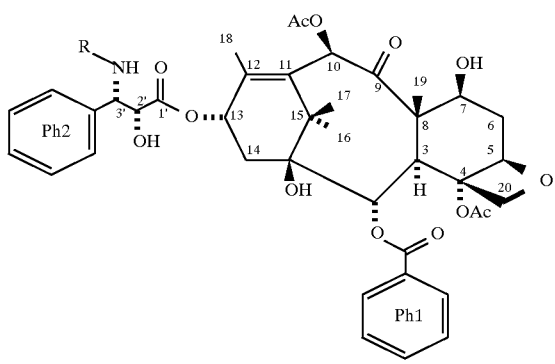
wherein R is selected from the group consisting of,
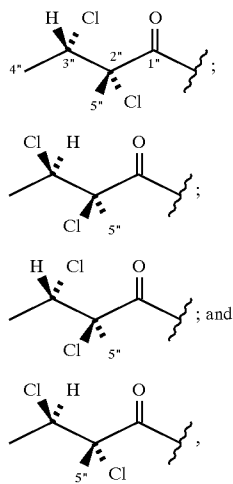

(I)

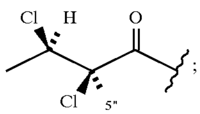

(II)

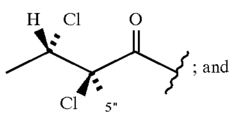

; and (III)

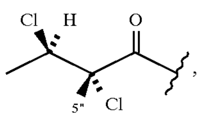

, (IV)

comprising chlorinating cephalomannine and/or 7-epi-cephalomannine under conditions effective to selectively chlorinate the unsaturated 2", 3" side-chain portion of cephalomannine and/or 7-epi-cephalomannine.

9. The method of claim 8 wherein a mixture of diastereomeric compounds I, II, III and IV is produced, and further comprising separating each of the compounds from the mixture.

10. The method of claim 8 wherein the cephalomannine and/or 7-epi-cephalomannine is present in a mixture in any amount comprising paclitaxel and other taxane ring compounds.

11. The method of claim 10, wherein the chlorination reaction is carried out at temperatures ranging from about −20° C. to about 20° C.

12. The method of claim 10, wherein the chlorination reaction is carried out at temperatures ranging from about −5° C. to about 5° C.

13. The method of claim 10, wherein the chlorination reaction is carried out in the dark.

14. The method of claim 10, wherein the chlorination reaction is carried out using a stoichiometric amount of chlorine relative to cephalomannine and/or 7-epi-cephalomannine concentration.

15. The method of claim 10, wherein the chlorination reaction is carried out using a solution of chlorine in a chlorinated solvent selected from the group consisting of $CCl_4$, $CHCl_3$, $ClCH_2CH_2Cl$ and $CH_2Cl_2$.

* * * * *